(12) United States Patent
Lyu et al.

(10) Patent No.: US 11,883,374 B2
(45) Date of Patent: *Jan. 30, 2024

(54) LACOSAMIDE PHARMACEUTICAL COMPOSITION AND DOSAGE FORM THEREOF

(71) Applicant: Shanghai Aucta Pharmaceuticals Co., Ltd., Shanghai (CN)

(72) Inventors: Shaoqiong Lyu, Shanghai (CN); Shoufeng Li, Basking Ridge, NJ (US); Xun Zheng, Shanghai (CN); Zhongqin Wang, Shanghai (CN)

(73) Assignee: SHANGHAI AUCTA PHARMACEUTICALS CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/664,513

(22) Filed: May 23, 2022

(65) Prior Publication Data

US 2022/0280456 A1    Sep. 8, 2022

Related U.S. Application Data

(60) Division of application No. 17/177,485, filed on Feb. 17, 2021, now Pat. No. 11,337,943, which is a continuation-in-part of application No. PCT/CN2020/094556, filed on Jun. 5, 2020.

(30) Foreign Application Priority Data

Jun. 6, 2019   (CN) .......................... 201910490175.8
Nov. 28, 2019  (CN) .......................... 201911189496.0

(51) Int. Cl.
    *A61K 9/16*     (2006.01)
    *A61K 31/165*   (2006.01)
    *A61K 9/50*     (2006.01)

(52) U.S. Cl.
    CPC .......... *A61K 31/165* (2013.01); *A61K 9/5047* (2013.01); *A61K 9/5078* (2013.01); *A61K 9/5084* (2013.01)

(58) Field of Classification Search
    None
    See application file for complete search history.

(56) References Cited

U.S. PATENT DOCUMENTS

| 2013/0251813 | A1  | 9/2013  | Cawello et al. |            |
|--------------|-----|---------|----------------|------------|
| 2018/0021307 | A1* | 1/2018  | Kaminski       | A61K 31/4015 |
|              |     |         |                | 514/423    |
| 2018/0161282 | A1  | 6/2018  | Nguyen et al.  |            |
| 2019/0054009 | A1  | 2/2019  | Cawello et al. |            |

FOREIGN PATENT DOCUMENTS

| CN | 102670544   | A   | 9/2012  |           |
|----|-------------|-----|---------|-----------|
| CN | 102885796   | A   | 1/2013  |           |
| CN | 102920663   | A   | 2/2013  |           |
| CN | 103561727   | A   | 2/2014  |           |
| CN | 105534949   | A   | 5/2016  |           |
| CN | 106619531   | A   | 5/2017  |           |
| EP | 3753554     | A1  | 12/2020 |           |
| WO | 2011101863  | A2  | 8/2011  |           |
| WO | WO-2011101863 | A2 * | 8/2011 | ........... A61K 9/2013 |
| WO | 2015120110  | A2  | 8/2015  |           |

\* cited by examiner

*Primary Examiner* — Susan T Tran
(74) *Attorney, Agent, or Firm* — FOX ROTHSCHILD LLP

(57) ABSTRACT

A dosage form of lacosamide and a pharmaceutical dosage form thereof is disclosed. The dosage form includes an extended release portion and optionally an immediate release portion. Also provided are methods of providing extended release of lacosamide and treatment of a neurological or psychiatric disease or condition.

19 Claims, 10 Drawing Sheets

LACOSAMIDE PHARMACEUTICAL COMPOSITION AND DOSAGE FORM THEREOF

CROSS-REFERENCE TO RELATED APPLICATIONS

This application is a continuation-in-part of International Application No. PCT/CN2020/094556, filed Jun. 5, 2020, which claims priority to Chinese Patent Application No. 201911189496.0, filed Nov. 28, 2019 and Chinese Patent Application No. 201910490175.8, filed Jun. 6, 2019, the contents of which are incorporated herein by reference in their entirety.

FIELD OF THE INVENTION

The present invention relates to a pharmaceutical composition of lacosamide and a pharmaceutical dosage form thereof, in particular to a pharmaceutical composition comprising lacosamide as an active ingredient and an extended release dosage form of lacosamide comprising the pharmaceutical composition.

BACKGROUND OF THE INVENTION

In the pharmaceutical field, extended release dosage forms are well-recognized and widely used. Extended release dosage forms have many significant clinical advantages, such as reducing frequency of administration and maintaining a stable blood drug level over an extended period of time. Oral extended release multiparticulate system has the technical characteristic of "dose distribution", such that the drug is distributed more homogeneously and absorbed more uniformly in the gastrointestinal tract.

Lacosamide is an anticonvulsant that has been approved in several countries for the treatment of partial onset seizure. Partial seizures occur when abnormal electrical activity begins in only one part of the brain. Partial-onset seizures include simple partial seizures, where a person remains fully aware and does not lose consciousness (such as muscle jerking or stiffening, or sense things that are not actually present), and complex partial seizures, where a person loses awareness, stares blankly, or may seem to be daydreaming (such as picking at their clothing or repeating words or phrases). Lacosamide is well tolerated in the treatment of epilepsy, and the daily dose can reach 200-400 mg/day. The most common side effects are dizziness, diplopia, headache and nausea. The high daily dose administered as immediate release dosage form would potentially cause a high incidence of adverse reactions. The incidence of side effects of lacosamide directly correlates with the maximum steady-state plasma concentration ($C_{max,ss}$) of lacosamide, and the efficacy of lacosamide in the treatment of epilepsy is mainly associated with the area under the steady-state plasma concentration-time curve ($AUC_{ss}$). The marketed dosage forms of lacosamide include immediate release tablets, oral solutions and intravenous solutions. The immediate release tablet (IR, Vimpat®) is administered twice daily, with specifications of 50 mg, 100 mg, 150 mg, and 200 mg. There are no marketed extended release dosage forms of lacosamide for once daily oral administration so far. Therefore, there is a clinical need to develop a novel dosage form of lacosamide for once daily oral administration, to reduce adverse reactions and improve patient compliance.

SUMMARY OF THE INVENTION

In the first aspect, the present invention provides a pharmaceutical composition of lacosamide, comprising extended release multiparticulates, wherein each of the extended release multiparticulates comprises:
(a) a drug-loaded core, comprising lacosamide or a pharmaceutically acceptable salt thereof; and
(b) an extended release layer coating the drug-loaded core, comprising a pH independent extended release agent.

In some embodiments, the drug-loaded core comprises an inert pellet core and an outer layer coating the inert pellet core, and the lacosamide or a pharmaceutically acceptable salt thereof is placed in the outer layer.

In some embodiments, the lacosamide or a pharmaceutically acceptable salt thereof is uniformly dispersed in the drug-loaded core.

In some embodiments, the lacosamide or a pharmaceutically acceptable salt thereof is released according to one or more of the following in vitro dissolutions (w/w): (a) 0.1-8% in 1 hour, (b) 2-25% in 2 hours, (c) 18-70% in 4 hours, and/or (d) 70-100% in 10 hours, 12 hours, 14 hours, 16 hours, or 20 hours, wherein the dissolution is determined using a USP (United States Pharmacopoeia) type 2 dissolution system (Paddle Apparatus) at 75 rpm and a temperature of 37±0.5° C. in a dissolution medium of 900 ml 0.1 N HCl.

In some embodiments, the lacosamide or a pharmaceutically acceptable salt thereof is released according to one or more of the following in vitro dissolutions (w/w): (a) less than 8% in 1 hour, (b) less than 12% in 2 hours, (c) less than 45% in 4 hours, and/or (d) more than 50% in 12 hours, wherein the dissolution is determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for at least 6 hours.

In some embodiments, the lacosamide or a pharmaceutically acceptable salt thereof accounts for about 40 wt % to about 80 wt % of the weight of the particulate.

In some embodiments, the extended release agent accounts for about 5 wt % to about 30 wt % of the weight of the particulate.

In some embodiments, the weight ratio of the lacosamide or a pharmaceutically acceptable salt thereof to the extended release agent is about 15:1 to about 1:1.

In some embodiments, the pharmaceutical composition of lacosamide comprises about 20 mg to about 600 mg of the lacosamide or a pharmaceutically acceptable salt thereof.

In some embodiments, the extended release agent is selected from the group consisting of ethyl cellulose, methyl cellulose, cellulose acetate, polyvinyl acetate, polyacrylate, ammonio methacrylate copolymer type A (ethyl acrylate/methyl methacrylate/trimethylamino ethyl methacrylate chloride copolymer (in a suitable ratio for example 1:2:0.2)), ammonio methacrylate copolymer type B (ethyl acrylate/methyl methacrylate/trimethylamino ethyl methacrylate chloride copolymer (in a suitable ratio for example 1:2:0.1)), ethyl acrylate/methyl methacrylate copolymer, and any mixtures thereof, and the like. In some embodiments, the extended release agent is pH independent. In some embodiments, the composition or dosage form described herein includes one, two, three or more pH independent extended release agents.

In some embodiments, the pharmaceutical composition of lacosamide further comprises an immediate release portion, wherein the lacosamide or a pharmaceutically acceptable salt thereof in the immediate release portion accounts for 1% to 40% (w/w) of the total amount of the lacosamide or a pharmaceutically acceptable salt thereof in the pharmaceutical composition.

In the second aspect, the present invention provides an extended release dosage form of lacosamide, comprising the pharmaceutical composition of lacosamide of the present invention, and in the form of a capsule, a sachet, a sprinkle, a caplet, a troche, a pouch, a tablet, or any other dosage form suitable for oral administration.

In the third aspect, the present invention provides an extended release dosage form of lacosamide, comprising an immediate release portion and an extended release portion, wherein the lacosamide or a pharmaceutically acceptable salt thereof in the immediate release portion accounts for 1% to 40% (w/w) of the total amount of the lacosamide or a pharmaceutically acceptable salt thereof in the dosage form.

In the fourth aspect, the present invention provides a method for the treatment of a neurological or psychiatric disease or condition, comprising administering to a subject in need thereof a therapeutically effective amount of the pharmaceutical composition of lacosamide or the extended release dosage form of lacosamide of the present invention.

In the fifth aspect, the present invention provides use of the pharmaceutical composition of lacosamide of the present invention in the manufacture of a medicament for the treatment of a neurological or psychiatric disease or condition.

In the sixth aspect, the present invention provides the pharmaceutical composition of lacosamide or the extended release dosage form of lacosamide of the present invention for use in the treatment of a neurological or psychiatric disease or condition.

In some embodiments, the disease or condition is selected from the group consisting of epilepsy, migraine, essential tremor, restless limb syndrome, cluster headache, neuralgia, neuropathic pain, Tourette's syndrome, infantile spasm, anxiety, bipolar disorder, psychosis, mania, schizophrenia, depression, dementia, autism, obsessive compulsive disorder, post-traumatic stress disorder, attention deficit hyperactivity disorder, impulse control disorder, borderline personality disorder, addiction, chronic neurodegenerative disorder, acute neurodegeneration, and amyotrophic lateral sclerosis. Preferably, the disease or condition is partial onset seizure.

In some embodiments, the pharmaceutical composition or dosage form is for once daily oral administration.

In some embodiments, the peak-trough fluctuation (PTF) of the pharmaceutical composition or dosage form is less than about 70%, less than about 60%, less than about 50%, less than about 40%, less than about 30%, less than about 20% or less than 15%.

In some embodiments, the PTF of the pharmaceutical composition or dosage form orally administered once daily is reduced by at least 15% compared to the immediate release dosage form Vimpat® orally administered at the same daily dose of lacosamide twice daily.

In some embodiments, the $AUC_{ss}$ and $C_{max,ss}$ of the pharmaceutical composition or dosage form orally administered once daily are 80% to 125% of those of the immediate release dosage form Vimpat® orally administered at the same daily dose of lacosamide twice daily.

DETAILED DESCRIPTION OF THE INVENTION

Figure 1:
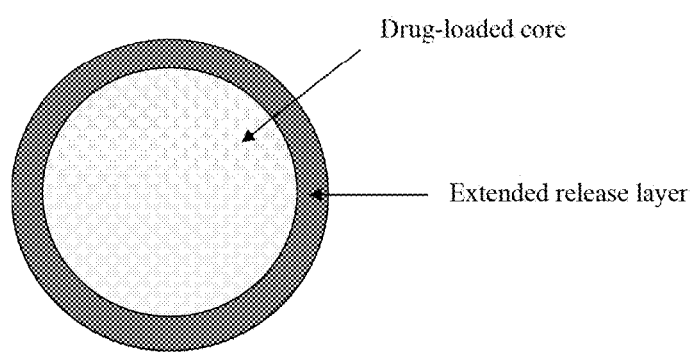
FIG. 1 depicts a particulate in which the active ingredient is dispersed in the drug-loaded core.

Various embodiments herein disclose extended release dosage forms of lacosamide or a pharmaceutically acceptable salt thereof. The dosage form can adjust the dissolution of active ingredients, reduce PTF and adverse reactions, without reducing the effectiveness.

Although the following contents may refer to or exemplify a specific embodiment of a pharmaceutical composition or dosage form, they are not limited to the specified ranges of the pharmaceutical composition or dosage form. In view of practicality and economy considerations, a person skilled in the art can make various modifications to, e.g., the content of active ingredients and the dosage regimen of the dosage form for treating diseases or disorders.

Unless otherwise defined, all technical and scientific terms used herein have the same meaning as commonly understood by a person skilled in the field of the present invention. In case of conflict, the definitions provided in the application prevail.

The term "a", "an" or "the" as used herein means "one or more" or "at least one". That is, reference to any element or composition of the present invention by "a", "an" or "the" does not exclude the possibility of the presence of a plurality of the elements and compositions.

The term "lacosamide", "active pharmaceutical ingredient", or "active ingredient" as used herein refers to the compound (R)-2-acetamido-N-benzyl-3-methoxypropionamide. The lacosamide in the pharmaceutical composition or dosage form described herein can be used in various pharmaceutically acceptable forms thereof, including but not limited to a salt, a hydrate, a polymorph, a co-crystal, an anhydride, an amorphous form, and a solvate thereof.

The term "extended release" or "ER" as used herein refers to extended release of an active pharmaceutical ingredient over an extended period of time, which is longer than about 2 hours, preferably longer than about 4 hours, more preferably longer than about 8 hours, more preferably longer than about 12 hours, more preferably longer than about 16 hours, up to longer than about 24 hours.

The term "immediate release" or "IR" as used herein refers to release of more than or equal to about 80% of an active pharmaceutical ingredient in less than or equal to about 1 hour. Typically, more than or equal to about 85% or more than or equal to about 90% of an active pharmaceutical ingredient in an immediate release dosage form is released in less than or equal to about 1 hour. In some embodiments, more than or equal to about 80% or more than or equal to about 90% or more than or equal to about 95% of an active pharmaceutical ingredient in an immediate release dosage form is released in less than or equal to about 30 minutes. In the application, during in vitro dissolution of the immediate release dosage form VIMPAT® (Lacosamide) Film Coated Tablet used as reference listed drug (RLD), more than 80% of lacosamide or a pharmaceutically acceptable salt thereof in the immediate release dosage form VIMPAT® is released in less than or equal to about 1 hour, wherein the dissolution is determined using a USP type 2 dissolution system (Paddle Apparatus) at 75 rpm and a temperature of 37±0.5° C. in a dissolution medium of 900 ml 0.1 N HCl.

In the present invention, "extended release portion" or "immediate release portion" refers to particulates that allow extended release or immediate release of an active pharmaceutical ingredient, or when the particulates have two-layer or multi-layer, extended release-immediate release structures, to particulate portions that allow extended release or immediate release of an active pharmaceutical ingredient.

When describing the "release" of a pharmaceutical composition or dosage form, it means that the pharmaceutical composition or dosage form is placed in an aqueous environment, and the active pharmaceutical ingredient contained therein leaves the pharmaceutical composition or dosage form to dissolve in the aqueous environment. Unless otherwise indicated, the amount of the active pharmaceutical ingredient released from the pharmaceutical composition or dosage form is measured by dissolution testing in aqueous medium as described herein. The results of the dissolution testing are reported in terms of percentage content (w/w) released within the release time.

The term "subject" refers to a mammal, and can be an animal or a human.

The term "comprise", "contain", "include", or "have" as used in the description and claims herein does not have a limiting meaning. Such terms should be understood to include a stated step or element, or group of steps or elements, but not exclude any other step or element, or group of steps or elements.

Unless otherwise indicated, the term "multiparticulate" or "multiparticulate system" as used herein refers to a system or combination containing many particulates, and these particulates can exist in any forms, including "pellets", "balls", "granules", "globules", "mini-tablets" or any structural units, without any limitations on the nature and size thereof.

The term "inert" as used herein refers to the action or influence of a substance, and the substance may or may not influence the bioavailability of the active pharmaceutical ingredient, but has no pharmaceutical activity by itself.

The term "about" and the like as used herein, when used in connection with a numerical variable, generally means that the value of the variable and all values of the variable are within the range of experimental error (e.g., within the 95% confidence interval for the mean) or within ±10% or within ±5% of the indicated value, whichever is greater.

The term "peak-trough fluctuation" or "PTF" as used herein is calculated as $100\%*(C_{max,ss}-C_{min,ss})/(AUC_{tau,ss}/tau)$, where $C_{max,ss}$ is the maximum steady-state plasma concentration of lacosamide, $C_{min,ss}$ is the minimum steady-state plasma concentration of lacosamide, $AUC_{tau,ss}$ is the area under the plasma concentration-time curve within a dosing interval tau under steady-state conditions, and tau is a dosing interval in hours, e.g., the pharmaceutical composition or extended release dosage form of the present invention is administered once daily, and the dosing interval is equal to 24 hours.

The term "pH independent" means that the nature of a substance does not depend on the pH value or is not affected by the pH value of the medium or solution.

The term "single dose" means that a subject has received a single dose of the drug formulation and the drug plasma concentration has not achieved steady state.

The term "steady state" means that the blood plasma concentration curve for a given drug does not substantially fluctuate after repeated doses to dose of the formulation.

"Eudragit RS100" described herein refers to ethyl acrylate/methyl methacrylate/trimethylamino ethyl methacrylate chloride copolymer (1:2:0.1), and "Eudragit RL100" refers to ethyl acrylate/methyl methacrylate/trimethylamino ethyl methacrylate chloride copolymer (1:2:0.2). The trade name, chemical composition and registered name of Eudragit products described herein are listed in the following table:

| Trade name | Chemical composition | Registered name |
| --- | --- | --- |
| Eudragit RL100 | Ethyl acrylate/m ethyl methacrylate/trimethylamino ethyl methacrylate chloride copolymer (1:2:0.2) | Ammonio methacrylate copolymer type A |
| Eudragit RS100 | Ethyl acrylate/methyl methacrylate/trimethylamino ethyl methacrylate chloride copolymer (1:2:0.1) | Ammonio methacrylate copolymer type B |

The present invention provides a pharmaceutical composition of lacosamide and a dosage form thereof for once daily oral administration. The pharmaceutical composition or dosage form controls the release of lacosamide or a pharmaceutically acceptable salt thereof at a certain rate, thereby reducing PTF, reducing side effects and ensuring the effectiveness of drugs.

Pharmaceutical Composition

In an aspect, the present invention provides a pharmaceutical composition of lacosamide, comprising extended release multiparticulates, wherein each of the extended release multiparticulates comprises:
(a) a drug-loaded core, comprising lacosamide or a pharmaceutically acceptable salt thereof; and
(b) an extended release layer coating the drug-loaded core, comprising a pH independent extended release agent, wherein the extended release layer is free from lacosamide or its pharmaceutically acceptable salt.

In a preferred embodiment, the drug-loaded core does not comprise an extended release agent.

In a preferred embodiment, the extended release layer does not comprise an active ingredient either. The pharmaceutical composition of the present invention is not a matrix forming pharmaceutical composition, and the active ingredient and the extended release agent are placed in separate layers, respectively, and are not mixed together. For example, both the extended release layers of the particulates shown in FIGS. 1 and 2 do not contain active ingredients.

In some embodiments, the lacosamide or a pharmaceutically acceptable salt thereof is uniformly dispersed in the drug-loaded core (as shown in FIG. 1).

Figure 2:
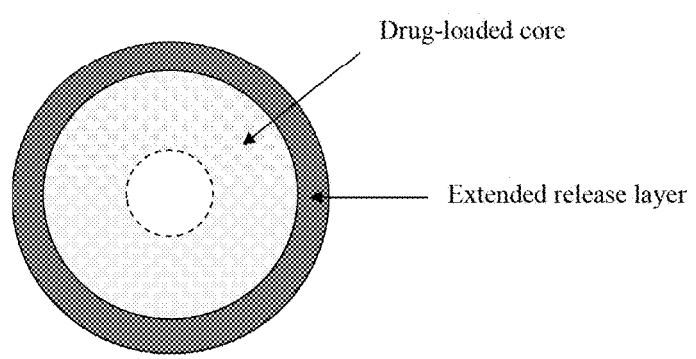
FIG. 2 depicts a particulate in which the active ingredient is dispersed in the outer layer coating the inert pellet core.

Alternatively, in some embodiments, the drug-loaded core comprises an inert pellet core (a core that does not contain an active ingredient) and an outer layer coating the inert pellet core, and the lacosamide or a pharmaceutically acceptable salt thereof is placed in the outer layer (as shown in FIG. 2).

In a preferred embodiment, each of the extended release multiparticulates further comprises an isolation layer between the drug-loaded core and the extended release layer.

In a preferred embodiment, each of the extended release multiparticulates further comprises a protective layer coating the extended release layer.

In some embodiments, an immediate release layer containing an active ingredient can be further coated outside the extended release layer, so that a certain amount of the active ingredient can be released immediately after administration. The added immediate release layer can be directly coated outside the extended release layer or can be coated outside the protective layer outside the extended release layer, and another protective layer can further be selectively coated outside the immediate release layer.

The drug-loaded core of the present invention can be prepared by various existing technologies known in the art, such as by extrusion spheronization, fluidized bed and tablet press. In some embodiments, the drug-loaded core comprises at least one or more filler(s), including but not limited to povidone (PVP), crospovidone (PVPP), lactose, mannitol, sugars, microcrystalline cellulose, calcium hydrophosphate, corn starch, starch, silicon dioxide, hydroxypropyl cellulose, etc.

In some embodiments, as shown in FIG. 2, the active ingredient is coated outside the inert pellet core. An isolation layer may optionally be further coated outside the active ingredient. The inert pellet core can be commercially available (such as sugar pellets, microcrystalline cellulose pellets, starch pellets, silicon dioxide pellets, etc.) or can be prepared by conventional methods (such as extrusion spheronization, fluidized bed, etc.).

In some embodiments, the particle size of the inert pellet core ranges from 100 μm-1500 μm, preferably 150 μm-1000 μm, more preferably 200 μm-700 μm, more preferably 300-600 μm, more preferably 300-500 μm. In some embodiments, the drug-loaded core comprises at least one or more binding agents. The active pharmaceutical ingredient (in the form of lacosamide or a pharmaceutically acceptable salt thereof) is mixed with at least one binding agent, and then coated on the inert pellet core. The binding agents include but are not limited to povidone (PVP), hydroxypropyl cellulose (HPC), methyl cellulose (MC), hydroxypropyl methyl cellulose (HPMC), sodium carboxymethyl cellulose, starch slurry, gelatin, arabic gum and mixtures thereof.

In some embodiments, the prepared extended release multiparticulates of lacosamide have an average particle size of from about 100 μm to about 3000 μm, from about 200 μm to about 2000 μm, from about 300 μm to about 1400 μm, preferably from about 500 μm to about 1400 μm, more preferably from about 600 μm to about 1400 μm, and most preferably from about 600 μm to about 1200 μm.

The active ingredient raw materials (lacosamide or a pharmaceutically acceptable salt thereof) used in this application have a particle size range (D90) of from about 0.1 μm to about 1000 μm, preferably from about 2 μm to about 200 μm, more preferably from about 2 μm to about 100 μm, and most preferably from about 2 μm to about 60 μm.

In some embodiments, the lacosamide or a pharmaceutically acceptable salt thereof is released according to one or more of the following in vitro dissolutions (w/w): (a) 0.1-8% in 1 hour, (b) 2-25% in 2 hours, (c) 18-70% in 4 hours, and/or (d) 70-100% in 10 hours, 12 hours, 14 hours, 16 hours, or 20 hours, wherein the dissolution is determined using a USP type 2 dissolution system (Paddle Apparatus) at 75 rpm and a temperature of 37±0.5° C. in a dissolution medium of 900 ml 0.1 N HCl.

In some embodiments, the lacosamide or a pharmaceutically acceptable salt thereof is released according to one or more of the following in vitro dissolutions (w/w): (a) less than 8% in 1 hour, (b) less than 12% in 2 hours, (c) less than 45% in 4 hours, and/or (d) more than 50% in 12 hours, wherein the dissolution is determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for at least 6 hours. Preferably, the lacosamide or a pharmaceutically acceptable salt thereof is released according to the following in vitro dissolution: (a) less than 6% in 1 hour, (b) less than 10% in 2 hours, and (c) less than 30% in 4 hours.

In some embodiments, the lacosamide or a pharmaceutically acceptable salt thereof is released according to one or more of the following in vitro dissolutions (w/w): (a) less than about 20% in 1 hour, (b) about 20%-80% in 4 hours, or (c) more than about 80% in 12 hours, wherein the dissolution is determined using a USP type 1 dissolution system (Basket Apparatus) at 100 rpm and a temperature of 37±0.5° C. in 900 ml of pH 6.8 phosphate buffer for 12 hours. Preferably, the lacosamide or a pharmaceutically acceptable salt thereof is released according to the following in vitro dissolution: (a) less than about 20% in 1 hour, (b) about 20%-80% in 4 hours, and (c) more than about 80% in 12 hours.

The extended release agent (material) in the extended release layer can control the dissolution of the active ingredient, and the dissolution of the particulates depends on the coating weight gain. The extended release agent can be prepared by a known synthetic route or directly commercially available. In some embodiments, the pH independent extended release agents include but are not limited to ethyl cellulose, methyl cellulose, cellulose acetate, polyvinyl acetate, polyacrylate, polymethacrylate, ammonio methacrylate copolymer type A (ethyl acrylate/methyl methacrylate/trimethylamino ethyl methacrylate chloride copolymer (1:2:0.2)), ammonio methacrylate copolymer type B (ethyl acrylate/methyl methacrylate/trimethylamino ethyl methacrylate chloride copolymer (1:2:0.1)), ethyl acrylate/methyl methacrylate copolymer, and any mixtures thereof, and the like. In some embodiments, the pH independent extended release agent is selected from the group consisting of Eudragit RS100 (ethyl acrylate/methyl methacrylate/trimethylamino ethyl methacrylate chloride copolymer (1:2:0.1)), Eudragit RL100 (ethyl acrylate/methyl methacrylate/trimethylamino ethyl methacrylate chloride copolymer (1:2:0.2)), and a combination thereof. In some embodiments, the pH independent extended release agent is a combination of Eudragit RS100 (ethyl acrylate/methyl methacrylate/trimethylamino ethyl methacrylate chloride copolymer (1:2:0.1)) and Eudragit RL100 (ethyl acrylate/methyl methacrylate/trimethylamino ethyl methacrylate chloride copolymer (1:2:0.2)), wherein the ratio of the Eudragit RS100 (ethyl acrylate/methyl methacrylate/trimethylamino ethyl methacrylate chloride copolymer (1:2:0.1)) to the Eudragit RL100 (ethyl acrylate/methyl methacrylate/trimethylamino ethyl methacrylate chloride copolymer (1:2:0.2)) is greater than or equal to 3:1, greater than or equal to 4:1, greater than or equal to 5:1, greater than or equal to 6:1, greater than or equal to 7:1, greater than or equal to 8:1, or greater than or equal to 9:1; optionally, the ratio of the Eudragit RS100 (ethyl acrylate/methyl methacrylate/trimethylamino ethyl methacrylate chloride copolymer (1:2:0.1)) to the Eudragit RL100 (ethyl acrylate/methyl methacrylate/trimethylamino ethyl methacrylate chloride copolymer (1:2:0.2)) is about 4:1, about 5:1, about 6:1, about 7:1, about 8:1, about 9:1, about 9.5:1 or about 9.9:1. In some embodiments, the pH independent extended release agent is Eudragit RS100 (ethyl acrylate/methyl methacrylate/trimethylamino ethyl methacrylate chloride copolymer (1:2:0.1)). In a preferred embodiment, the pH independent extended release agent is selected from ethyl cellulose, and its viscosity specifications include but are not limited to ethyl cellulose 7 cP, ethyl cellulose 10 cP, ethyl cellulose 20 cP, and ethyl cellulose 100 cP, preferably, the viscosity specification of ethyl cellulose is 7 cP.

In some embodiments, the extended release agent accounts for about 2% to about 50%, about 5% to about 50%, about 5% to about 40%, about 5% to about 30%, about 7% to about 30%, about 8% to about 30%, about 8% to about 25%, about 10% to about 25%, about 10% to about 20%, or about 20% to about 30% of the particulate weight (w/w). In some embodiments, the extended release agent accounts for about 8 wt % to about 30 wt % of the weight of the particulate. In a specific embodiment, the extended release agent is Eudragit RS100, and accounts for about 8 wt % to about 30 wt % of the weight of the particulate.

In some embodiments, the extended release agent accounts for about 5% to about 20%, about 5% to about 15%, about 5% to about 10%, about 5% to about 9%, about 5% to about 8%, about 5% to about 7%, or about 5% to about 6% of the particulate weight (w/w). In some embodiments, the extended release agent accounts for about 5 wt % to about 15 wt % of the weight of the particulate. In a specific embodiment, the extended release agent is ethyl cellulose, and accounts for about 5 wt % to about 15 wt % of the weight of the particulate.

In some embodiments, the weight ratio of lacosamide or a pharmaceutically acceptable salt thereof to its extended release agent is about 15:1 to about 1:1, about 15:1 to about 2:1, about 10:1 to about 2:1, about 8:1 to about 2:1, about 8:1 to about 3:1, about 10:1 to about 4:1, about 6:1 to about 3:1, about 5:1 to about 2:1. Non-limiting exemplary ratios include about 10:1, about 9:1, about 8:1, about 7:1, about 6:1, about 5:1, about 4:1, about 3:1, about 10:1, or about 1:1. Preferably, the weight ratio of lacosamide or a pharmaceutically acceptable salt thereof to an extended release agent is about 8:1 to about 3:1. In a specific embodiment, the extended release agent is Eudragit RS100, and the weight ratio of lacosamide or a pharmaceutically acceptable salt thereof to the extended release agent is about 8:1 to about 3:1.

In some embodiments, the weight ratio of lacosamide or a pharmaceutically acceptable salt thereof to its extended release agent is about 12:1 to about 2:1, about 12:1 to about 5:1, about 12:1 to about 6:1, about 12:1 to about 7:1, about 12:1 to about 8:1, about 12:1 to about 9:1, or about 12:1 to about 10:1. Preferably, the weight ratio of lacosamide or a pharmaceutically acceptable salt thereof to an extended release agent is about 12:1 to about 5:1. In a specific embodiment, the extended release agent is ethyl cellulose, and the weight ratio of lacosamide or a pharmaceutically acceptable salt thereof to the extended release agent is about 12:1 to about 5:1.

In some embodiments, the pharmaceutical composition of lacosamide is for once daily oral administration. In some embodiments, the pharmaceutical composition of lacosamide comprises about 1 mg to about 1000 mg, about 20 mg to about 600 mg, about 40 mg to about 200 mg, about 50 mg to about 300 mg, about 50 mg to about 600 mg of the lacosamide or a pharmaceutically acceptable salt thereof.

In a preferred embodiment, the pharmaceutical composition of lacosamide comprises about 50 mg, about 100 mg, about 150 mg, about 200 mg, about 300 mg, or about 400 mg of the lacosamide.

In some embodiments, when the weight ratio of lacosamide or a pharmaceutically acceptable salt thereof to an extended release agent (e.g., Eudragit RS®) is about 8:1 to about 3:1, the extended release time for the pharmaceutical composition or dosage form to release the active ingredient in an aqueous medium is about 2 hours to about 24 hours, about 4 hours to about 24 hours, about 8 hours to about 24 hours, about 4 hours to about 12 hours, about 12 hours to about 24 hours, about 8 hours to about 12 hours, or about 12 hours to about 18 hours.

In some embodiments, the extended release layer may further comprise one or more plasticizers, including but not limited to diethyl phthalate, triethyl citrate, dibutyl sebacate, polyethylene glycol, triacetin, tributyl citrate, glycerol, and propylene glycol.

In some embodiments, the extended release layer may further comprise one or more pore forming agents, including but not limited to polyethylene glycol, hydroxypropyl methyl cellulose, hydroxypropyl cellulose, and polyvinyl pyrrolidone. In a preferred embodiment, the pore forming agent is hydroxypropyl methyl cellulose. The selection of different pore forming agents in the extended release layer would affect the amount of the extended release agent, and a lower amount of the extended release agent would result in poor process stability. For the pharmaceutical composition of lacosamide of the present application, the applicant found that an appropriate amount of the extended release agent can be controlled by selecting hydroxypropyl methyl cellulose as the pore forming agent, which achieves better process stability.

In some embodiments, the pore forming agent accounts for about 20%-80% of the weight of the extended release agent. In some embodiments, the pore forming agent accounts for about 25%-75% of the weight of the extended release agent. In some embodiments, the pore forming agent accounts for about 30%-70% of the weight of the extended release agent. In some embodiments, the pore forming agent accounts for about 40%-70% of the weight of the extended release agent. In a preferred embodiment, the pore forming agent accounts for about 50%-65% of the weight of the extended release agent. In a preferred embodiment, the pore forming agent accounts for about 50%-60% of the weight of the extended release agent. In a specific embodiment, the extended release agent is ethyl cellulose, the pore forming agent is hydroxypropyl methylcellulose, and the pore forming agent accounts for about 50%-60% of the weight of the extended release agent.

In some embodiments, the extended release layer may further comprise water soluble small molecule agents, e.g., sugar or reducing sugar, lactose, sucrose, mannitol, sorbitol, and the like.

In some embodiments, the materials of the isolation layer or protective layer that can be optionally used may be commercially available, including but not limited to opadry (Opadry®), talcum, magnesium stearate, hydroxypropyl methyl cellulose, hydroxypropyl cellulose, and the like.

In some embodiments, in each of the multiparticulates, the average weight percentage of lacosamide or a pharmaceutically acceptable salt thereof is at least 20%, at least 25%, at least 30%, at least 35%, at least 38%, at least 45%, at least 50%, up to 80%, up to 75%, or up to 70%. In some embodiments, in each of the multiparticulates, the average weight percentage of lacosamide or a pharmaceutically acceptable salt thereof is about 50% to about 60%. In some embodiments, the lacosamide or a pharmaceutically acceptable salt thereof accounts for about 30% to about 90%, about 40% to about 80%, about 50% to about 70%, or about 50% to about 60% of the weight of the particulate.

In some embodiments, the inert pellet core is a microcrystalline cellulose pellet with a particle size of 300-500 μm. The lacosamide is mixed with the binding agent PVP K30, and then coated on the inert pellet core. The Eudragit RS® is used as the extended release agent in the extended release layer, and accounts for 10%-25% of the weight of the particulate. In some embodiments, an isolation layer containing Opadry® is coated on the drug-loaded core to smoothen the surface of the drug-loaded core. In some embodiments, a protective layer containing Opadry® can be further coated outside the extended release layer of the particulate to reduce friction between the particulates or to mask any unfavorable taste or smell.

In some embodiments, the inert pellet core is a microcrystalline cellulose pellet with a particle size of 300-500 μm. The lacosamide is mixed with the binding agent povidone (PVP K30), and then coated on the inert pellet core. Ethyl cellulose is used as the extended release agent in the extended release layer, and accounts for 5%-15% of the weight of the particulate. Hydroxypropyl methyl cellulose is used as the pore forming agent in the extended release layer, and accounts for about 50%-60% of the weight of the extended release agent. In some embodiments, an isolation layer containing opadry (Opadry®) is coated on the drug-loaded core to smoothen the surface of the drug-loaded core. In some embodiments, a protective layer containing opadry (Opadry) can be further coated outside the extended release layer of the particulate to reduce friction between the particulates or to mask any unfavorable taste or smell.

Although the present invention mainly describes a pharmaceutical composition of lacosamide comprising extended release multiparticulates, the pharmaceutical composition of the present invention may also comprise a combination of an extended release portion and an immediate release portion. Specifically, in some embodiments, all lacosamide or a pharmaceutically acceptable salt thereof in the pharmaceutical composition is made extended release, and the pharmaceutical composition does not comprise an immediate release portion. In some embodiments, an immediate release portion is introduced into the pharmaceutical composition and combined with the extended release portion, while the pharmaceutical composition can still allow the lacosamide or a pharmaceutically acceptable salt thereof to release over an extended period of time, and the immediate release portion provides an initial burst release of the drug such that the therapeutic blood concentration level is reached faster. The lacosamide or a pharmaceutically acceptable salt thereof comprised in the immediate release portion accounts for a percentage of about 1% to about 50%, about 5% to about 45%, about 5% to about 40%, about 10% to about 40%, about 15% to about 40%, about 15% to about 30%, about 15% to about 20%, about 1% to about 40%, about 1% to about 30%, about 1% to about 20%, about 1% to about 10%, about 10% to about 30%, about 10% to about 20%, about 10% to about 15%, or about 5% to about 10% (w/w) of the total amount of the lacosamide or a pharmaceutically acceptable salt thereof in the pharmaceutical composition.

In some embodiments, the pharmaceutical composition of lacosamide further comprises an immediate release portion, wherein the lacosamide or a pharmaceutically acceptable salt thereof in the immediate release portion accounts for 1% to 40% (w/w) of the total amount of the lacosamide or a pharmaceutically acceptable salt thereof in the pharmaceutical composition; preferably, wherein the lacosamide or a pharmaceutically acceptable salt thereof in the immediate release portion accounts for 1% to 35% (w/w) of the total amount of the lacosamide or a pharmaceutically acceptable salt thereof in the pharmaceutical composition; preferably, wherein the lacosamide or a pharmaceutically acceptable salt thereof in the immediate release portion accounts for 10% to 30% (w/w) of the total amount of the lacosamide or a pharmaceutically acceptable salt thereof in the pharmaceutical composition.

In some embodiments, the lacosamide or a pharmaceutically acceptable salt thereof comprised in the immediate release portion of the pharmaceutical composition accounts for about 1% to about 35% (w/w) of the total amount of the lacosamide or a pharmaceutically acceptable salt thereof in the pharmaceutical composition; preferably about 5% to about 30% (w/w). Accordingly, the lacosamide or a pharmaceutically acceptable salt thereof comprised in the extended release portion of the pharmaceutical composition accounts for about 65% to about 99% (w/w) of the total amount of the lacosamide or a pharmaceutically acceptable salt thereof in the pharmaceutical composition; preferably about 70% to about 95% (w/w). In some embodiments, the lacosamide or a pharmaceutically acceptable salt thereof comprised in the extended release portion accounts for about 65% to about 70%, about 70% to about 75%, about 75% to about 80%, about 80% to about 85%, about 85% to about 90%, about 90% to about 95%, about 70% to about 80%, about 80% to about 90%, or about 90% to about 95% (w/w) of the total amount of the lacosamide or a pharmaceutically acceptable salt thereof in the pharmaceutical composition. The lacosamide or a pharmaceutically acceptable salt thereof comprised in the immediate release portion accounts for the remaining percentage of the total amount of the lacosamide or a pharmaceutically acceptable salt thereof in the pharmaceutical composition subtracting the lacosamide or a pharmaceutically acceptable salt thereof in the extended release portion. Preferably, the lacosamide or a pharmaceutically acceptable salt thereof comprised in the extended release portion accounts for about 99%, about 95%, about 90%, about 85%, about 80%, about 75%, about 70% or about 65% (w/w) of the total amount of the lacosamide or a pharmaceutically acceptable salt thereof in the pharmaceutical composition, and the lacosamide or a pharmaceutically acceptable salt thereof comprised in the immediate release portion accounts for about 1%, about 5%, about 10%, about 15%, about 20%, about 25%, about 30% or about 35% (w/w) of the total amount of the lacosamide or a pharmaceutically acceptable salt thereof in the pharmaceutical composition. The lacosamide or a pharmaceutically acceptable salt thereof comprised in the immediate (extended) release portion accounts for the remaining percentage of the total amount of the lacosamide or a pharmaceutically acceptable salt thereof in the pharmaceutical composition subtracting the lacosamide or a pharmaceutically acceptable salt thereof in the extended (immediate) release portion. Generally, PTF can be reduced by extended release of a drug. For the lacosamide extended release multiparticulates of the present application, the applicant has further surprisingly found that PTF can be further reduced by combining the extended release multiparticulates of lacosamide with an immediate release portion in a certain ratio, compared to the case where no immediate release portion is included.

In some embodiments, the extended release portion and the immediate release portion are physically connected or independent of each other.

In some embodiments, the extended release portion and the immediate release portion can be physically connected together to form a two-layer structure or a multi-layer structure. For example, in some embodiments, an immediate release layer containing an active ingredient can be further coated outside the extended release layer, so that a certain amount of the active ingredient can be released immediately after administration. The added immediate release layer can be directly coated outside the extended release layer or can be coated outside the protective layer outside the extended release layer, and another protective layer can further be selectively coated outside the immediate release layer.

In some embodiments, the extended release portion and the immediate release portion are independent of each other, and do not need to be physically connected to each other. For example, in some embodiments, the immediate release portion can be in the form of a single unit, or in the form of multiparticulates, the dosage form method of which can be the same as that of the extended release multiparticulates except that the particulates are not coated with an extended release layer. The extended release multiparticulates and the immediate release multiparticulates can be mixed into the same capsules. In a preferred embodiment, the immediate release portion consists of multiparticulates, e.g., the immediate release portion consists of drug-loaded particulates that are not coated with an extended release layer.

In some embodiments, the prepared immediate release multiparticulates of lacosamide have an average particle size of from about 300 μm to about 1200 μm, preferably from about 500 μm to about 1200 μm, more preferably from about 600 μm to about 1200 μm, and most preferably from about 600 μm to about 1000 μm.

In some embodiments, the lacosamide or a pharmaceutically acceptable salt thereof in a pharmaceutical composition comprising a combination of an extended release portion and an immediate release portion is released according to one or more of the following in vitro dissolutions (w/w): (a) about 10%-30% in 1 hour, (b) about 30%-90% in 4 hours, or (c) more than about 90% in 12 hours, wherein the dissolution is determined using a USP type 1 dissolution system (Basket Apparatus) at 100 rpm and a temperature of 37±0.5° C. in 900 ml of pH 6.8 phosphate buffer for 12 hours. Preferably, the lacosamide or a pharmaceutically acceptable salt thereof is released according to the following in vitro dissolution: (a) about 10%-28% in 1 hour, (b) about 28%-90% in 4 hours, and (c) more than about 90% in 12 hours. More Preferably, the lacosamide or a pharmaceutically acceptable salt thereof is released according to the following in vitro dissolution: (a) about 11%-18% in 1 hour, (b) about 20%-35% in 2 hours, (c) about 40%-70% in 4 hours and (d) more than about 90% in 12 hours. More Preferably, the lacosamide or a pharmaceutically acceptable salt thereof is released according to the following in vitro dissolution: (a) about 11%-18% in 1 hour, (b) about 20%-35% in 2 hours, (c) about 45%-65% in 4 hours, and (d) about 72%-92% in 6 hours and (e) more than about 90% in 12 hours Dosage Form In another aspect, the present invention provides an extended release dosage form of lacosamide or a pharmaceutical composition thereof described herein. The dosage form can be in the form of a capsule, a sachet, a sprinkle, a caplet, a troche, a pouch, a tablet, or any other dosage form suitable for oral administration. Preferably, the dosage form is a capsule, a sachet, or a sprinkle.

In some embodiments, the dosage form is for once daily oral administration.

In some embodiments, a unit dosage form comprises about 20 mg to about 600 mg of the lacosamide or a pharmaceutically acceptable salt thereof. In some embodiments, a unit dosage form comprises about 50 mg, about 100 mg, about 150 mg, about 200 mg, about 300 mg, or about 400 mg of the lacosamide. In some embodiments, a unit dosage form is in the form of a capsule.

In a preferred embodiment, the dosage form is a capsule. The pharmaceutical composition of the present invention can be encapsulated in a suitable shell, e.g., a capsule of any suitable size, such as a size 000, 00, 0el, 0, 1, 2, 3, 4 or 5 capsule. A single capsule comprises about 1 mg to about 1000 mg, about 20 mg to about 600 mg, about 40 mg to about 200 mg, about 50 mg to about 300 mg, about 50 mg to about 600 mg of the lacosamide or a pharmaceutically acceptable salt thereof. More preferably, a single capsule comprises about 50 mg, about 100 mg, about 150 mg, about 200 mg, about 300 mg or about 400 mg of the lacosamide or a pharmaceutically acceptable salt thereof.

The dosage form generally includes an extended release portion, comprising:
(a) a core comprising lacosamide or a pharmaceutically acceptable salt thereof, and
(b) an extended release layer enclosing the core, wherein the extended release layer is free from lacosamide or a pharmaceutically acceptable salt thereof and comprises an extended release agent which is pH independent;
wherein the core is free from the extended release agent.

In some embodiments, the weight ratio of lacosamide or a pharmaceutically acceptable salt thereof to its extended release agent is about 15:1 to about 1:1, about 15:1 to about 2:1, about 10:1 to about 2:1, about 8:1 to about 2:1, about 8:1 to about 3:1, about 10:1 to about 4:1, about 6:1 to about 3:1, about 5:1 to about 2:1. Non-limiting exemplary ratios include about 10:1, about 9:1, about 8:1, about 7:1, about 6:1, about 5:1, about 4:1, about 3:1, about 10:1, or about 1:1.

In some embodiments, the extended release agent ranges from about 5% to about 40% from, about 5% to about 30%, from about 10% to about 20%, or from about 15% to about 20% by weight in the extended release portion.

In some embodiments, the extended release dosage form includes an immediate release portion and an extended release portion, wherein the lacosamide or a pharmaceutically acceptable salt thereof in the immediate release portion accounts for 1% to 40% (w/w) of the total amount of the lacosamide or a pharmaceutically acceptable salt thereof in the dosage form; preferably, wherein the lacosamide or a pharmaceutically acceptable salt thereof in the immediate release portion accounts for 1% to 35% (w/w) of the total amount of the lacosamide or a pharmaceutically acceptable salt thereof in the dosage form; preferably, wherein the lacosamide or a pharmaceutically acceptable salt thereof in the immediate release portion accounts for 5% to 30% (w/w) of the total amount of the lacosamide or a pharmaceutically acceptable salt thereof in the dosage form; preferably, wherein the lacosamide or a pharmaceutically acceptable salt thereof in the immediate release portion accounts for 10% to 30% (w/w) of the total amount of the lacosamide or a pharmaceutically acceptable salt thereof in the dosage form. In exemplary embodiments, the immediate release portion accounts for about 5%, about 8%, about 10%, about 12%, about 15%, about 20%, about 25%, or about 30% by weight of the total amount of the lacosamide or a pharmaceutically acceptable salt thereof in the dosage form.

In some embodiments, the lacosamide or a pharmaceutically acceptable salt thereof in the extended release portion accounts for about 65% to about 70%, about 70% to about 75%, about 75% to about 80%, about 80% to about 85%, about 85% to about 90%, about 90% to about 95%, about 70% to about 80%, about 80% to about 90%, or about 90% to about 95% (w/w) of the total amount of the lacosamide or a pharmaceutically acceptable salt thereof in the dosage form, while the remainder is disposed in the immediate release portion.

In some embodiments, the total amount of lacosamide or a pharmaceutically acceptable salt thereof is at least 20%, at least 25%, at least 30%, at least 35%, at least 38%, at least 45%, at least 50%, up to 80%, up to 75%, or up to 70% by weight in the dosage form. In some embodiments, the total amount of lacosamide or a pharmaceutically acceptable salt thereof accounts for about 30% to about 90%, about 40% to about 80%, about 50% to about 70%, about 60% to about 70%, or about 50% to about 60% of the weight of dosage form.

In some embodiments, the core comprises an inert pellet inner core (a core that does not contain an active ingredient) and an outer layer enclosing the inert pellet inner core, and the lacosamide or a pharmaceutically acceptable salt thereof is placed in the outer layer (as shown in FIG. 2).

In some embodiments, the immediate release portion is coated outside the extended release portion, optionally with an isolation layer between the two portions. The immediate release portion first releases lacosamide therein before the extended release portion releases lacosamide in a controlled release manner. There may also be an isolation layer between the extended release layer and the core containing lacosamide. The combination (the immediate release portion enclosing the extended release portion) can be in any suitable form, including for example a tablet or a particulate. In some embodiments, the dosage form contains a plurality of such particulates. In some embodiments, the dosage form is a capsule enclosing plurality of particulates, each of which includes the immediate release portion coated outside the extended release portion. A single capsule can enclose for example, more than 5, more than 10, more then 20, more than 30, more than 40, more than 50, more than 80, or more than 100 particulates.

In some embodiments, the particles disclosed herein have an average particle size of from about 300 μm to about 1500 μm, preferably from about 500 μm to about 1300 μm, more preferably from about 500 μm to about 1200 μm, and most preferably from about 600 μm to about 1200 μm. Non-limiting examples of average particle size or average diameter of the particles include about 200 μm, about 300 μm, about 400 μm, about 500 μm, about 600 μm, about 700 μm, about 800 μm, about 900 μm, about 1000 μm, about 1100 μm, about 1200 μm, about 1400 μm, or about 1500 μm.

In some embodiments, the immediate release portion or the extended release portion consists of multiparticulates, and the immediate release portion consists of drug-loaded particulates that are not coated with an extended release layer. In exemplary embodiments, the immediate release portion and the extended release portion are each in the form of multiparticulates, wherein the multiparticulates of the extended release portion are free from the immediate release portion and the multiparticulates of the immediate release portion are free from the extended release portion. The multiparticulates of the immediate release portion and the multiparticulates of the extended release portion can be mixed in a single unit dosage form (e.g. capsule) for administration to a subject in need thereof.

The amount of the extended release can be adjusted depending on the specific agent and the intended release or dissolution. In some embodiments, the extended release agent accounts for about 2% to about 50%, about 5% to about 50%, about 5% to about 40%, about 5% to about 30%, about 7% to about 30%, about 7% to about 25%, about 7% to about 20%, about 7% to about 15%, about 8% to about 30%, about 8% to about 25%, about 10% to about 25%, about 10% to about 20%, or about 20% to about 30% of the dosage form or the particulate by weight (w/w). Additional examples of the amount of the extended release agent include about 5%, about 6%, about 7%, about 8%, about 9%, about 10%, about 11%, about 12%, about 13%, about 14%, about 15%, about 16%, about 20%, about 25%, about 30%, about 35%, about 40%, about 45%, or about 50% by weight.

In some embodiments, the dosage form is configured so that when the dissolution profile is determined using a USP type 2 dissolution system (Paddle Apparatus) at 75 rpm and a temperature of 37±0.5° C. in 900 ml 0.1 N HCl, the lacosamide pharmaceutical composition or lacosamide extended release dosage form of the present invention has one or more or all of the following in vitro dissolution characteristics of the active ingredient (lacosamide or a pharmaceutically acceptable salt thereof):

(a) in 1 hour, the released active ingredient accounts for about 0.1% to about 20%, about 0.1% to about 15%, about 0.1% to about 12%, about 0.1% to about 10%, about 0.1% to about 8%, about 0.1% to about 6%, about 0.1% to about 5%, about 0.1% to about 4%, about 0.1% to about 3%, about 0.1% to about 2%, about 0.5% to about 20%, about 0.5% to about 15%, about 0.5% to about 12%, about 0.5% to about 10%, about 0.5% to about 8%, about 0.5% to about 6%, about 0.5% to about 5%, about 0.5% to about 4%, about 0.5% to about 3%, about 1% to about 20%, about 1% to about 15%, about 1% to about 12%, about 1% to about 10%, about 1% to about 8%, about 1% to about 6%, about 1% to about 5%, about 1% to about 4%, or about 1% to about 3% of the total amount (w/w);

(b) in 2 hours, the released active ingredient accounts for about 2% to about 40%, about 2% to about 30%, about 2% to about 25%, about 2% to about 20%, about 2% to about 15%, about 2% to about 10%, about 2% to about 8%, about 5% to about 40%, about 5% to about 30%, about 5% to about 25%, about 5% to about 20%, about 5% to about 15%, about 5% to about 10%, about 8% to about 40%, about 8% to about 30%, about 8% to about 25%, about 8% to about 20%, about 8% to about 15%, or about 8% to about 12% of the total amount (w/w);

(c) in 4 hours, the released active ingredient accounts for about 15% to about 90%, about 18% to about 90%, about 20% to about 80%, about 18% to about 80%, about 18% to about 70%, about 18% to about 60%, about 18% to about 50%, about 18% to about 40%, about 18% to about 30%, about 25% to about 90%, about 25% to about 80%, about 25% to about 70%, about 25% to about 60%, about 25% to about 50%, about 25% to about 40%, about 25% to about 35%, or about 25% to about 30% of the total amount (w/w); and/or (d) in 10 hours, 12 hours, 14 hours, 16 hours or 20 hours, the released active ingredient accounts for about 50% to about 100%, about 70% to about 100%, about 60% to about 100%, about 50% to about 95%, about 70% to about 95%, or about 80% to about 100% of the total amount (w/w). In some embodiments, the pharmaceutical composition or dosage form has one, two, three or four of the above dissolution characteristics. In some embodiments, the pharmaceutical composition or dosage form provides the dissolution of the active ingredient having the above (a). In some embodiments, the pharmaceutical composition or dosage form provides the dissolution of the active ingredient having the above (a) and (b). In some embodiments, the pharmaceutical composition or dosage form provides the dissolution of the active ingredient having the above (a), (b) and (c). In some embodiments, the pharmaceutical composition or dosage form provides the dissolution of the active ingredient having the above (a), (b), (c) and (d).

In some embodiments, the pharmaceutical composition or dosage form has the following in vitro dissolution for the release of the active ingredient: about 0.1% to about 8% is released in 1 hour, about 2% to about 25% is released in 2 hours, about 18% to about 70% is released in 4 hours, and/or about 70% to about 100% is released in 10 hours. The dissolution is determined using a USP type 2 dissolution system (Paddle Apparatus) at 75 rpm and a temperature of 37±0.5° C. in a dissolution medium of 900 ml 0.1 N HCl.

In some embodiments, the pharmaceutical composition or dosage form has the following in vitro dissolution for the release of the active ingredient: about 0.1% to about 8% is released in 1 hour, about 2% to about 14% is released in 2 hours, about 20% to about 70% is released in 4 hours, and/or about 70% to about 100% is released in 10 hours. The dissolution is determined using a USP type 2 dissolution system (Paddle Apparatus) at 75 rpm and a temperature of 37±0.5° C. in a dissolution medium of 900 ml 0.1 N HCl.

In some embodiments, the lacosamide pharmaceutical composition or lacosamide extended release dosage form of the present invention has one or more of the following in vitro dissolution characteristics of the active ingredient (lacosamide or a pharmaceutically acceptable salt thereof):
(a) the released active ingredient is less than 10%, less than 8%, less than 6%, less than 5% or less than 4% in 1 hour;
(b) the released active ingredient is less than 20%, less than 15%, less than 12%, less than 10%, less than 8%, less than 6% or less than 4% in 2 hours;
(c) the released active ingredient is less than 50%, less than 45%, less than 40%, less than 35%, less than 30%, less than 25%, less than 20%, less than 15% or less than 10% in 4 hours; and/or
(d) the released active ingredient is more than 40%, more than 50%, more than 60%, more than 70% or more than 80% in 12 hours.

The dissolution is determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for at least 6 hours (up to 12 hours or 18 hours or 24 hours). In some embodiments, the pharmaceutical composition or dosage form provides the dissolution of the active ingredient having the above (a) and (b). In some embodiments, the pharmaceutical composition or dosage form provides the dissolution of the active ingredient having the above (a), (b) and (c). In some embodiments, the pharmaceutical composition or dosage form provides the dissolution of the active ingredient having the above (a), (b) and (d). In some embodiments, the pharmaceutical composition or dosage form provides the dissolution of the active ingredient having the above (a), (b), (c) and (d).

In some typical embodiments, the lacosamide pharmaceutical composition or lacosamide extended release dosage form of the present invention has one or more of the following in vitro dissolution characteristics of the active ingredient (lacosamide or a pharmaceutically acceptable salt thereof): (a) the released active ingredient is less than 8% in 1 hour, (b) the released active ingredient is less than 12% in 2 hours, (c) the released active ingredient is less than 45% in 4 hours, and/or (d) the released active ingredient is more than 50% in 12 hours, wherein the dissolution is determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for 6 hours, 12 hours or 18 hours. In some embodiments, the extended release agent is a pH independent extended release agent. In some embodiments, the lacosamide or a pharmaceutically acceptable salt of the pharmaceutical composition or dosage form of the present invention is released according to the above (a), (a)+(b), (a)+(d), (a)+(b)+(c), (a)+(b)+(d), or (a)+(b)+(c)+(d).

In some typical embodiments, the lacosamide pharmaceutical composition or lacosamide extended release dosage form of the present invention has one or more of the following in vitro dissolution characteristics of the active ingredient (lacosamide or a pharmaceutically acceptable salt thereof): (a) the released active ingredient is less than 6% in 1 hour, (b) the released active ingredient is less than 10% in 2 hours, (c) the released active ingredient is less than 30% in 4 hours, and/or (d) the released active ingredient is more than 50% in 12 hours, wherein the dissolution is determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for 6 hours, 12 hours or 18 hours. In some embodiments, the extended release agent is a pH independent extended release agent. In some embodiments, the lacosamide or a pharmaceutically acceptable salt of the pharmaceutical composition or dosage form of the present invention is released according to the above (a), (a)+(b), (a)+(d), (a)+(b)+(c), (a)+(b)+(d), or (a)+(b)+(c)+(d).

In some typical embodiments, the lacosamide pharmaceutical composition or lacosamide extended release dosage form of the present invention has one or more of the following in vitro dissolution characteristics of the active ingredient (lacosamide or a pharmaceutically acceptable salt thereof): (a) the released active ingredient is less than 4% in 1 hour, (b) the released active ingredient is less than 8% in 2 hours, (c) the released active ingredient is less than 20% in 4 hours, and/or (d) the released active ingredient is more than 50% in 12 hours, wherein the dissolution is determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for 6 hours, 12 hours or 18 hours. In some embodiments, the extended release agent is a pH independent extended release agent. In some embodiments, the lacosamide or a pharmaceutically acceptable salt of the pharmaceutical composition or dosage form of the present invention is released according to the above (a), (a)+(b), (a)+(d), (a)+(b)+(c), (a)+(b)+(d), or (a)+(b)+(c)+(d).

In some typical embodiments, the lacosamide pharmaceutical composition or lacosamide extended release dosage form of the present invention has one or more of the following in vitro dissolution characteristics of the active ingredient (lacosamide or a pharmaceutically acceptable salt thereof): (a) the released active ingredient is less than 4% in 1 hour, (b) the released active ingredient is less than 8% in 2 hours, (c) the released active ingredient is less than 40% in 4 hours, and/or (d) the released active ingredient is more than 50% in 12 hours, wherein the dissolution is determined using a USP type 1 dissolution system (Basket Apparatus) at 100 rpm and a temperature of 37±0.5° C. in 900 ml of pH 1.0 HCl/34 mM NaCl buffer for 2 hours, then in 900 ml of pH 6.8 phosphate/100 mM NaCl buffer using the same dissolution system, rotation speed and temperature for 4 hours, and then in 900 ml of pH 7.5 phosphate/100 mM NaCl buffer using the same dissolution system, rotation speed and temperature for 6 hours, 12 hours or 18 hours. In some embodiments, the extended release agent is a pH independent extended release agent. In some embodiments, the lacosamide or a pharmaceutically acceptable salt of the pharmaceutical composition or dosage form of the present invention is released according to the above (a), (a)+(b), (a)+(d), (a)+(b)+(c), (a)+(b)+(d), or (a)+(b)+(c)+(d). Preferably, the lacosamide or a pharmaceutically acceptable salt thereof is released according to the following in vitro dissolution: (a) less than 4% in 1 hour, (b) less than 8% in 2 hours, (c) less than 40% in 4 hours, and (d) more than 50% in 12 hours.

In some typical embodiments, the lacosamide pharmaceutical composition or dosage form of the present invention is configured so that it has one or more of the following in vitro dissolution characteristics of the active ingredient (lacosamide or a pharmaceutically acceptable salt thereof): (a) the released active ingredient is about 10%-20%, about 11%-18%, about 12%-16%, about 11%-16% or about 12%-15% (e.g. about 10%, about 11%, about 12%, about 13%, about 14%, about 15%, about 16%, about 17%, about 18%, about 19%, or about 20%) of the total amount of the active ingredient in the dosage form in 1 hour, (b) the released active ingredient is about 15%-40%, about 16%-38%, about 20%-35% or about 22%-33% (e.g. about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36, about 37% or about 38%) in 2 hours, (c) the released active ingredient is about 30%-70%, about 32%-70%, about 40%-70%, about 40-65% or about 45%-65% (e.g. about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, or about 68%) in 4 hours, (d) the released active ingredient is about 65%-95%, about 68%-94%, about 72%-90% or about 75%-90% (e.g. about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or about 91%) in 6 hours, and/or (e) the released active ingredient is more than 80%, more than 85%, more than 90%, or more than 95% in 12 hours, wherein the dissolution is determined using a USP type 1 dissolution system (Basket Apparatus) at 100 rpm and a temperature of 37±0.5° C. in 900 ml of pH 6.8 phosphate buffer for 12 hours. In some embodiments, the extended release agent is a pH independent extended release agent. In some embodiments, lacosamide or a pharmaceutically acceptable salt of the pharmaceutical composition or dosage form of the present invention is released according to the above (a), (a)+(b), (a)+(d), (a)+(b)+(c), (a)+(b)+(d), (a)+(b)+(c)+(d), or (a)+(b)+(c)+(d)+(e). In some embodiments, the dissolution is determined using a USP type 2 dissolution system (Paddle Apparatus) at 75 rpm and a temperature of 37±0.5° C. in a dissolution medium of 900 ml 0.1 N HCl.

In some embodiments, the amount of lacosamide or a pharmaceutically acceptable salt thereof dissolved between $6^{th}$ hour and $8^{th}$ hour ranges from about 5% to about 15%, from about 7% to about 15%, from about 10% to about 15%, or from about 5% to about 12% of the total amount of lacosamide or a pharmaceutically acceptable salt thereof in the dosage form. Non-limiting examples of lacosamide or a pharmaceutically acceptable salt thereof dissolved between $6^{th}$ hour and $8^{th}$ hour include about 5%, about 6%, about 7%, about 8%, about 9%, about 10%, about 11%, about 12%, about 13%, about 14%, and about 15%.

Different from delayed release, the dosage form disclosed herein can provide a desirable amount of lacosamide or a pharmaceutically acceptable salt thereof within a short period of time. In some embodiments, more than 2%, more than 3%, more than 4%, more than 5%, more than 6%, more than 8%, or more than 10% of lacosamide or a pharmaceutically acceptable salt thereof is dissolved from the dosage from as measured with a USP type 1 dissolution system (Basket Apparatus) at 100 rpm and a temperature of 37±0.5° C. in 900 ml of pH 6.8 phosphate buffer for 12 hours.

In some embodiments, the amount of lacosamide or a pharmaceutically acceptable salt dissolved in the first two hours is about 1.3-3.5 times, about 1.5-3.5 times, about 1.7-3.5 times, about 1.5-3 times, about 1.5-2.5 times, about 1.5-2.2 times, about 1.5-2.0 times, about 1.5-1.9 times, about 1.7-2.3 times, or about 2-2.5 times more than the amount dissolved in the first one hour. In some exemplary embodiments, the amount of lacosamide or a pharmaceutically acceptable salt dissolved in the first two hours is about 1.3, 1.5, 1.6, 1.7, 1.8, 1.9, 2.0, 2.1, 2.2, 2.4, 2.6, 2.8 or 3 times more than the amount dissolved in the first one hour. In some embodiments, the amount of lacosamide or a pharmaceutically acceptable salt dissolved in the first four hours is about 1.3-3.5 times, about 1.5-3.5 times, about 1.7-3.5 times, about 1.5-3 times, about 1.5-2.5 times, about 1.6-2.2 times, about 1.7-2.3 times, about 1.7-2.2 times, or about 2-2.5 times more than the amount dissolved in the first two hours. In some exemplary embodiments, the amount of lacosamide or a pharmaceutically acceptable salt dissolved in the first four hours is about 1.3, 1.5, 1.7, 1.8, 1.9, 2.0, 2.1, 2.2, 2.3, 2.4, 2.6, 2.8 or 3 times more than the amount dissolved in the first two hours. In some embodiments, the amount of lacosamide or a pharmaceutically acceptable salt dissolved in the first six hours is about 1.3-3.5 times, about 1.5-3.5 times, about 1.7-3.5 times, about 1.5-3 times, about 1.5-2.5 times, about 1.6-2.2 times, about 1.7-2.3 times, about 1.7-2.2 times, or about 2-2.5 times more than the amount dissolved in the first three hours. In some exemplary embodiments, the amount of lacosamide or a pharmaceutically acceptable salt dissolved in the first six hours is about 1.3, 1.5, 1.7, 1.8, 1.9, 2.0, 2.1, 2.2, 2.3, 2.4, 2.6, 2.8 or 3 times more than the amount dissolved in the first three hours. In some embodiments, the amount of lacosamide or a pharmaceutically acceptable salt dissolved in the first two hours is about 1.5-2.2 times more than the amount dissolved in the first one hour, and the amount of lacosamide or a pharmaceutically acceptable salt dissolved in the first four hours is about 1.6-2.2 times more than the amount dissolved in the first two hours, and the amount of lacosamide or a pharmaceutically acceptable salt dissolved in the first six hours is about 1.6-2.2 times more than the amount dissolved in the first three hours. In some exemplary embodiments, the amount of lacosamide or a pharmaceutically acceptable salt thereof dissolved in the first two hours is about 1.5-2.0 times more than the amount dissolved in the first one hour, and the amount of lacosamide or a pharmaceutically acceptable salt thereof dissolved in the first four hours is about 1.7-2.2 times more than the amount dissolved in the first two hours, and the amount of lacosamide or a pharmaceutically acceptable salt thereof dissolved in the first six hours is about 1.7-2.2 times more than the amount dissolved in the first three hours.

In some embodiments, the dosage form described herein achieves more than 95%, more than 96%, more than 97%, more than 98%, or more than 99% of the AUC of an immediate release reference listed drug (RLD) of the same dosage. In some exemplary embodiments, the dosage form described herein when orally administered as single dose achieves more than 95%, more than 96%, more than 97%, more than 98%, or more than 99% of the AUC(0-inf) of immediate release dosage form VIMPAT® (Lacosamide) Film Coated Tablet of the same daily dosage when orally administered twice daily to a subject in fasting conditions.

In some embodiments, the immediate release portion encloses the extended release portion to form a particulate, and the dosage form contains a plurality of the particulates, which can be enclosed in any suitable form such as a capsule.

The extended release agents for the dosage form are as described above. In some embodiments, the dosage form includes one, two, three, or more extended release agents. In some embodiments, the pH independent extended release agent is selected from ethyl cellulose, and its viscosity specifications include but are not limited to ethyl cellulose 7 cP, ethyl cellulose 10 cP, ethyl cellulose 20 cP, and ethyl cellulose 100 cP, preferably, the viscosity specification of ethyl cellulose is 7 cP. In some embodiments, the dosage form includes only one extended release agent. In some embodiment, the extended release agent consists of ethyl cellulose.

In some embodiments, the dosage form is administered once a day, twice a day or as needed. In some embodiments, the dosage form contains lacosamide only in its salt free form. In some embodiments, the dosage form contains only extended release portion of lacosamide. In some embodiments, the dosage form contains an extended release portion of lacosamide and an immediate release portion of lacosamide.

In another aspect, the present invention also provides a kit comprising an immediate release portion and an extended release portion. The two portions can be mixed together or separated from each other. The ratio of the two portions may be the same as that in the above-mentioned pharmaceutical composition or dosage form. For example, in some embodiments, the lacosamide or a pharmaceutically acceptable salt thereof in the extended release portion accounts for about 65% to about 70%, about 70% to about 75%, about 75% to about 80%, about 80% to about 85%, about 85% to about 90%, about 90% to about 95%, about 70% to about 80%, about 80% to about 90%, or about 90% to about 95% (w/w) of the total amount of the lacosamide or a pharmaceutically acceptable salt thereof in the kit. The lacosamide or a pharmaceutically acceptable salt thereof in the immediate release portion accounts for the remaining percentage of the total amount of the lacosamide or a pharmaceutically acceptable salt thereof in the kit. In some embodiments, the kit comprises the above prepared extended release particulates and immediate release particulates. Both types of the particulates can be encapsulated in the same capsule or container.

Treatment Method and Use

Another aspect provides a method of providing an extended release of lacosamide in a subject, comprising administering to the subject a dosage form described herein, wherein the extended release corresponds to an in-vitro dissolution of the dosage form, wherein the dosage form is configured so that the total amount of lacosamide or a pharmaceutically acceptable salt thereof in the dosage form (including extended release portion and immediate release portion) dissolves during the in-vitro dissolution according to one or more or all of the following:
(a) from about 11% to about 18% in 1 hour,
(b) from about 20% to about 35% in 2 hours,
(c) from about 40% to about 70% in 4 hours,
(c) from about 65% to about 95% in 6 hours, and
(e) more than about 90% in 12 hours.
wherein the in-vitro dissolution is determined using a USP type 1 dissolution system (Basket Apparatus) at 100 rpm and a temperature of 37±0.5° C. in 900 ml of pH 6.8 phosphate buffer for 12 hours.

In some embodiments, the in-vitro dissolution satisfies the following:
(a) from about 11% to about 18% in 1 hour,
(b) from about 20% to about 35% in 2 hours,
(c) from about 45% to about 65% in 4 hours,
(c) from about 72% to about 92% in 6 hours, and
(e) more than about 90% in 12 hours.

In some embodiments, the immediate release portion of lacosamide or a pharmaceutically acceptable salt thereof ranges from about 8% to about 12% by weigh in the total amount of the extended release portion and the immediate release portion of lacosamide or a pharmaceutically acceptable salt thereof.

In some embodiments, the immediate release portion encloses the extended release portion in the dosage form, which contains a plurality of the particulates. In some embodiments, the dosage form is a capsule containing a plurality of the particulates.

In some embodiments, the extended release portion is in the form a first particulate and the immediate release portion is in the form a second particulate. The first particulate contains lacosamide or a pharmaceutically acceptable salt for only extended release. The second particulate contains lacosamide or a pharmaceutically acceptable salt for only immediate release. A plurality of the first particulates are admixed with a plurality of the second particulates in the dosage form. In some embodiments, the dosage from is administered once a day or twice a day.

Another aspect provides a method of achieving more than 90%, more than 95% or more than 98% of AUC(0-inf) of immediate released reference lacosamide orally administered twice a day to a subject in fasting condition. The method includes administering to the subject once a day the dosage form described herein, wherein the immediate released reference lacosamide dosage form (administered once or twice a day) and the dosage form described herein have the same daily dosage. In some embodiment, the dosage form of this invention is administered in a single dose and the immediate released reference lacosamide is administered for a single day dosage before comparison of their AUC. In some embodiment, a steady state has been reached for the dosage form of this invention of the present invention and the immediate released reference lacosamide before the comparison of their AUC.

In some embodiments, the method achieves more than 96%, more than 97%, more than 98%, or more than 99% of AUC(0-inf) of immediate released reference lacosamide.

In some embodiments, the dosage form provides an in-vitro dissolution of lacosamide according to one or more or all of the following:
(a) from about 11% to about 18% in 1 hour,
(b) from about 20% to about 35% in 2 hours,
(c) from about 45% to about 65% in 4 hours,
(d) from about 72% to about 92% in 6 hours, and
(e) more than about 90% in 12 hours,
wherein the in-vitro dissolution is determined using a USP type 1 dissolution system (Basket Apparatus) at 100 rpm and a temperature of 37±0.5° C. in 900 ml of pH 6.8 phosphate buffer for 12 hours. In some embodiments, the dissolution satisfies all of the above (a)-(e).

In some embodiments, the in-vitro dissolution is further characterized by one or more or all of the following:
the amount of lacosamide or a pharmaceutically acceptable salt thereof dissolved from the dosage form within first two hours is about 1.5-2.0 times more than the amount dissolved within first one hour; the amount of lacosamide or a pharmaceutically acceptable salt thereof dissolved within first four hours is about 1.7-2.2 times more than the amount dissolved within first two hours, and the amount of lacosamide or a pharmaceutically acceptable salt thereof dissolved within first six hours is about 1.7-2.2 times more than the amount dissolved within first three hours.

In another aspect, the present invention provides a method for the treatment of a neurological or psychiatric disease or condition, comprising administering to a subject in need thereof a therapeutically effective amount of the pharmaceutical composition of lacosamide or the dosage form described herein.

In another aspect, the present invention provides use of the pharmaceutical composition of lacosamide of the present invention in the manufacture of a medicament for the treatment of a neurological or psychiatric disease or condition.

In another aspect, the present invention provides the pharmaceutical composition of lacosamide or the dosage form described herein for use in the treatment of a neurological or psychiatric disease or condition.

In some embodiments, the disease or condition includes but is not limited to epilepsy, migraine, essential tremor, restless limb syndrome, cluster headache, neuralgia, neuropathic pain, Tourette's syndrome, infantile spasm, anxiety, bipolar disorder, psychosis, mania, schizophrenia, depression, dementia, autism, obsessive compulsive disorder, posttraumatic stress disorder, attention deficit hyperactivity disorder, impulse control disorder, borderline personality disorder, addiction, chronic neurodegenerative disorder, acute neurodegeneration, and amyotrophic lateral sclerosis. Preferably, the disease or condition is partial onset seizure.

Epileptic seizures are mainly of two types: partial seizures and generalized seizures. Partial seizures can again be of three type; i.e. simple partial, complex partial and partial with secondarily generalized tonic clonic seizure. Generalized seizures are classified as absence seizure, myoclonic seizure and tonic-clonic seizure.

Other examples of the disease or condition to be treated with the dosage form disclosed herein include anxiety disorder, allodynia, motoneuron disorder, acute and chronic pain (e.g. rheumatic inflammatory pain), central neuropathic pain, peripheral neuropathic pain, neuropathic trigeminal pain, bone cancer pain and/or chemotherapy-induced pain, and conditions associated with cortical spreading depression (CSD).

In some embodiments, the pharmaceutical composition or dosage form is orally administered once daily.

The lacosamide pharmaceutical composition or lacosamide extended release dosage form of the present invention can adjust the in vivo release of active ingredients and reduce peak-trough fluctuation (PTF). In some embodiments, the PTF of the pharmaceutical composition or dosage form is less than about 70%, less than about 60%, less than about 50%, less than about 40%, less than about 35%, or less than about 30%. In a preferred embodiment, the PTF of the pharmaceutical composition or dosage form is less than about 60%.

In some embodiments, the PTF of the pharmaceutical composition or dosage form orally administered once daily is reduced by at least 5%, at least 10%, at least 15%, at least 20%, or at least 25% compared to the immediate release dosage form Vimpat® orally administered at the same daily dose of lacosamide twice daily, preferably, the PTF is reduced by at least 15%.

In some embodiments, the $AUC_{ss}$ and $C_{max,ss}$ of the pharmaceutical composition or dosage form orally administered once daily are 75% to 125% of those of the immediate release dosage form Vimpat® orally administered at the same daily dose of lacosamide twice daily. In some embodiments, the $AUC_{ss}$ and $C_{max,ss}$ of the pharmaceutical composition or dosage form orally administered once daily are 80% to 125% of those of the immediate release dosage form Vimpat® orally administered at the same daily dose of lacosamide twice daily.

Lacosamide or a pharmaceutically composition thereof or a dosage form thereof disclosed herein may be administered to the subject by any suitable means. Non-limiting examples of methods of administration include, among others, administration though oral pathways, which includes administration in capsule, tablet, granule, pill, or other suitable forms.

The therapeutically effective amount of lacosamide required as a dose will depend on the route of administration, the type of subject, including human, being treated, and the physical characteristics of the specific subject under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions can be chosen by the individual physician in view of the patient's condition. (see e.g., Fingl et al. 1975, in "The Pharmacological Basis of Therapeutics", which is hereby incorporated herein by reference in its entirety, with particular reference to Ch. 1, p. 1).

In some embodiments, the dose range of lacosamide administered to the subject or patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In some embodiments, the composition or dosage form is administered 1 to 4 times per day. As will be understood by those of skill in the art, in certain situations it may be necessary to administer lacosamide or its dosage form disclosed herein in amounts that exceed, or even far exceed, the above-stated, preferred dosage range in order to effectively and aggressively treat particularly aggressive diseases or infections. In some embodiments, lacosamide or its dosage form will be administered for a period of continuous therapy, for example for a week or more, or for months or years.

In some embodiments, the oral pharmaceutical compositions described herein may be administered in single or divided doses, from one to four times a day. The oral dosage forms may be conveniently presented in unit dosage forms and prepared by any methods well known in the art of pharmacy.

Lacosamide or its dosage form can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of lacosamide or its dosage form in humans.

Lacosamide or its dosage form thereof may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising the compound of Formula I, or a pharmaceutically acceptable salt thereof formulated in a compatible pharmaceutical carrier may also be prepared, placed in an appropriate container, and labeled for treatment of an indicated condition.

The present invention is further illustrated by the following examples, but the scope of the present invention is not limited to these examples.

Example 1—Dosage Form of Extended Release Mini-Tablets

The formulations of extended release mini-tablets are shown in table 1.

TABLE 1

The formulations of extended release mini-tablets of Example 1.

| Ingredient (mg) | Formulation | | | | | |
|---|---|---|---|---|---|---|
| | E1-1-1 | E1-1-2 | E1-1-3 | E1-2-1 | E1-2-2 | E1-2-3 |
| | Batch number | | | | | |
| | 20180514-1(a)-1-1 | 20180514-1(a)-1-2 | 20180514-1(a)-1-3 | 20180514-2(a)-1-1 | 20180514-2(a)-1-2 | 20180514-2(a)-1-3 |
| | Immediate release mini-tablet | | | | | |
| Lacosamide | 200.0 | 200.0 | 200.0 | 200.0 | 200.0 | 200.0 |
| Povidone | 15.0 | 15.0 | 15.0 | 15.0 | 15.0 | 15.0 |
| Lactose Monohydrate | 79.0 | 79.0 | 79.0 | — | — | — |

TABLE 1-continued

The formulations of extended release mini-tablets of Example 1.

| Ingredient (mg) | Formulation | | | | | |
|---|---|---|---|---|---|---|
| | E1-1-1 | E1-1-2 | E1-1-3 | E1-2-1 | E1-2-2 | E1-2-3 |
| | Batch number | | | | | |
| | 20180514-1(a)-1-1 | 20180514-1(a)-1-2 | 20180514-1(a)-1-3 | 20180514-2(a)-1-1 | 20180514-2(a)-1-2 | 20180514-2(a)-1-3 |
| Calcium Hydrogen Phosphate | — | — | — | 79.0 | 79.0 | 79.0 |
| Silicon Dioxide | 3.0 | 3.0 | 3.0 | 3.0 | 3.0 | 3.0 |
| Magnesium Stearate | 3.0 | 3.0 | 3.0 | 3.0 | 3.0 | 3.0 |
| Extended release coating (EC:HPMC = 75:25 solution) | | | | | | |
| Ethyl Cellulose (EC) | 8.06 | 10.71 | 16.04 | 8.06 | 10.71 | 16.04 |
| Hydroxypropyl Methyl Cellulose (HPMC) | 2.69 | 3.57 | 5.35 | 2.69 | 3.57 | 5.35 |

The mini-tablet cores were prepared by direct compression on a single-punch tablet press with 3 mm round punches. Ethyl cellulose (EC) and hydroxypropyl methyl cellulose were dissolved in ethanol/water to prepare an extended release coating solution, and then the coating solution was coated on the mini-tablet cores. The in vitro dissolution was determined using a USP type 1 dissolution system (Basket Apparatus) at 100 rpm and a temperature of 37±0.5° C. in a dissolution medium of 500 ml of 0.1 N HCl for 24 hours. The dissolution samples were analyzed by high performance liquid chromatography (HPLC). The dissolution data of the formulations in Example 1 are shown in table 2.

TABLE 2

The dissolution data of the extended release mini-tablets of Example 1.

| Time, h | (%) | | | | | |
|---|---|---|---|---|---|---|
| | E1-1-1 20180514-1(a)-1-1 | E1-1-2 20180514-1(a)-1-2 | E1-1-3 20180514-1(a)-1-3 | E1-2-1 20180514-2(a)-1-1 | E1-2-2 20180514-2(a)-1-2 | E1-2-3 20180514-2(a)-1-3 |
| 0 | 0.0 | 0.0 | 0.0 | 0.0 | 0.0 | 0.0 |
| 1 | 0.1 | 0.0 | 0.0 | 0.3 | 0.1 | 0.0 |
| 2 | 0.5 | 0.2 | 0.0 | 0.8 | 0.4 | 0.1 |
| 3 | 1.2 | 0.4 | 0.1 | 1.8 | 0.9 | 0.2 |
| 4 | 2.8 | 0.8 | 0.2 | 3.7 | 1.5 | 0.4 |
| 6 | 6.9 | 2.1 | 0.6 | 8.5 | 4.2 | 0.9 |
| 9 | 13.8 | 5.6 | 2.2 | 16.7 | 9.7 | 3.1 |
| 12 | 21.8 | 9.5 | 5.1 | 26.0 | 16.0 | 6.2 |
| 16 | 33.9 | 15.2 | 9.5 | 40.2 | 25.2 | 10.9 |
| 20 | 47.8 | 21.6 | 14.2 | 55.4 | 35.0 | 16.0 |
| 24 | 62.9 | 28.8 | 19.4 | 71.3 | 45.7 | 21.5 |

Example 2—Dosage Form of Multiparticulates by Extrusion Spheronization

The formulations for preparing multiparticulates by extrusion spheronization are shown in table 3.

TABLE 3

The formulations for preparing multiparticulates by extrusion spheronization of Example 2.

| | Formulation | | |
|---|---|---|---|
| | E2-1 | E2-2 | E2-3 |
| | Batch number | | |
| Ingredient | 20180424-1d (gram/batch) | 20180424-2d (gram/batch) | 20180424-3d (gram/batch) |
| Lacosamide | 80.0 | 80.0 | 80.0 |
| Microcrystalline Cellulose | 10.0 | 8.0 | 18.0 |
| Crospovidone | 10.0 | 10.0 | 10.0 |
| Povidone | — | 2.0 | 2.0 |
| Water | q.s. | q.s. | q.s. |
| Drug load (w/w) | 80.0% | 80.0% | 72.7% |
| Sieve mesh | | 0.8 mm | |
| Extrusion speed | | 25 rpm | |
| Spheronization speed | | 800 rpm | |

Lacosamide together with microcrystalline cellulose, crospovidone, and povidone were added into a wet granulator. After mixing uniformly, an appropriate amount of water was added under stirring to obtain a wet soft material. The wet soft material was transferred into an extruder and extruded under the conditions of 0.8 mm sieve mesh and an extrusion speed of 25 rpm. The column-shaped wet extrudate was placed inside the spheronizer and spheronized for 1-3 minutes at a spheronization speed of 800 rpm, and then the resulting pellets were dried at 50° C. with the loss on drying (LOD) of less than 3%. The dried pellets were sieved, and the pellets between 20-30 mesh sieve were collected.

Example 3—Dosage Form of Multiparticulates by Extrusion Spheronization

The formulations for preparing multiparticulates by extrusion spheronization are shown in table 4.

TABLE 4

The formulations for preparing multiparticulates by extrusion spheronization of Example 3.

| | Formulation | | |
|---|---|---|---|
| | E3-1 | E3-2 | E3-3 |
| | Batch number | | |
| Ingredient | 20180502-2d (gram/batch) | 20180502-1d (gram/batch) | 20180503-1d (gram/batch) |
| Lacosamide | 73.4 | 70.0 | 66.6 |
| Microcrystalline Cellulose | 10.8 | 10.8 | 10.8 |
| Lactose Monohydrate | 3.4 | 6.8 | 10.2 |
| Povidone | 0.7 | 0.7 | 0.7 |
| Crospovidone | 10.0 | 10.0 | 10.0 |
| Water | q.s. | q.s. | q.s. |
| Drug load | 74.4% | 71.2% | 67.8% |
| Sieve mesh | | 0.8 mm | |
| Extrusion speed | | 25 rpm | |
| Spheronization speed | | 800 rpm | |

Lacosamide together with microcrystalline cellulose, lactose monohydrate, crospovidone, and povidone were added into a wet granulator. After mixing uniformly, an appropriate amount of water was added under stirring to obtain a wet soft material. The wet soft material was transferred into an extruder and extruded under the conditions of 0.8 mm sieve mesh and an extrusion speed of 25 rpm. The column-shaped wet extrudate was placed inside the spheronizer and spheronized for 1-3 minutes at a spheronization speed of 800 rpm, and then the resulting pellets were dried at 50° C. with the loss on drying (LOD) of less than 3%. The dried pellets were sieved, and the pellets between 20-30 mesh sieve were collected.

Example 4—Dosage Form of Extended Release Multiparticulates by Fluidized Bed Coating The formulations for preparing extended release multiparticulates by fluidized bed coating are shown in table 5.

TABLE 5

The formulations for preparing extended release multiparticulates by fluidized bed coating of Example 4.

| Composition | | Formulation (mg) | | | |
|---|---|---|---|---|---|
| | | E4-1 | E4-2 | E4-3 | E4-4 |
| Drug-loaded core | Microcrystalline Cellulose Pellet | 49.70 | 49.70 | 49.70 | 49.70 |
| | Lacosamide | 200.00 | 200.00 | 200.00 | 200.00 |
| | Povidone | 20.00 | 20.00 | 20.00 | 20.00 |
| | Ethanol | —* | —* | —* | —* |
| Isolation layer | Opadry | 4.32 | 4.32 | 4.32 | 4.32 |
| | Purified Water | —* | —* | —* | —* |
| Extended release layer | Ethyl Cellulose | 7.04 | 17.86 | 24.11 | 37.21 |
| | Polyethylene Glycol | 4.69 | 11.90 | 16.06 | 24.80 |
| | 95% Ethanol | —* | —* | —* | —* |

Note:
—* Solvent, evaporating during the process

A suspension of lacosamide and povidone was used as the drug coating solution, and the drug coating solution was uniformly coated on an inert microcrystalline cellulose pellet by using a fluidized bed, to achieve a desired drug loading level. An Opadry isolation layer was coated on the drug-loaded pellet, and then an extended release coating solution consisting of ethyl cellulose and polyethylene glycol was coated on the surface of the drug-loaded pellet, to obtain a desired different level of coating weight gain. The inlet airflow rate and the material temperature were adjusted to prevent spray drying of the coating solution or too wet pellets. The particle size of the prepared pellets was about 600 μm to about 1200 μm.

Figure 3:
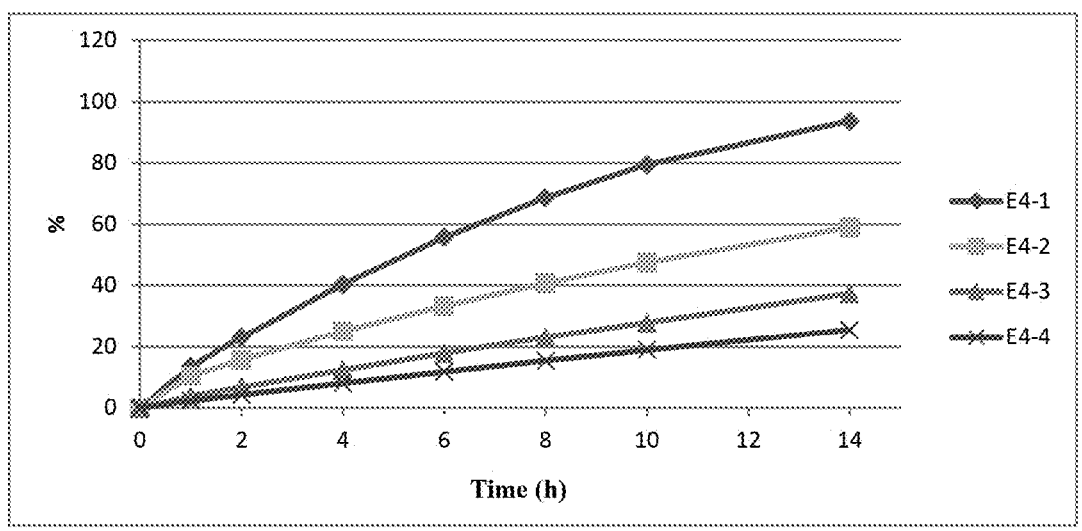
FIG. 3 illustrates the release characteristics of dissolution of the extended release multiparticulates of Example 4.

The in vitro dissolution was determined using a USP type 2 dissolution system (Paddle Apparatus) at 75 rpm and a temperature of 37±0.5° C. in a dissolution medium of 900 ml 0.1 N HCl. The dissolution samples were analyzed by high performance liquid chromatography (HPLC). The dissolution data of the four formulations in Example 4 are shown in table 6 and FIG. 3.

TABLE 6

The dissolution data of the extended release multiparticulates of Example 4.

| Time, hour | (%) | | | |
| --- | --- | --- | --- | --- |
| | E4-1 | E4-2 | E4-3 | E4-4 |
| 0 | 0.0 | 0.0 | 0.0 | 0.0 |
| 1 | 13.5 | 10.3 | 3.7 | 2.2 |
| 2 | 23.0 | 15.6 | 6.7 | 4.2 |
| 4 | 40.3 | 25.0 | 12.3 | 8.0 |
| 6 | 55.6 | 33.3 | 17.8 | 11.7 |
| 8 | 68.7 | 40.7 | 23.0 | 15.3 |
| 10 | 79.5 | 47.5 | 27.9 | 18.8 |
| 14 | 93.7 | 58.9 | 37.3 | 25.5 |

Example 5—Dosage Form of Extended Release Multiparticulates by Fluidized Bed Coating The formulations for preparing extended release multiparticulates by fluidized bed coating are shown in table 7.

TABLE 7

The formulations for preparing extended release multiparticulates by fluidized bed coating of Example 5.

| Composition | Formulation | E5-1 | E5-2 |
| --- | --- | --- | --- |
| Drug-loaded core | Microcrystalline Cellulose Pellet | 50.93 | 50.93 |
| | Lacosamide | 200.00 | 200.00 |
| | Povidone | 20.00 | 20.00 |
| | Ethanol | —* | —* |
| Extended release layer | Cellulose Acetate | 8.72 | 19.53 |
| | Polyethylene Glycol | 3.74 | 8.37 |
| | Acetone | —* | —* |
| | Water | —* | —* |

Note:
—* Solvent, evaporating during the process

A suspension of lacosamide and povidone was used as the drug coating solution, and the drug coating solution was uniformly coated on an inert microcrystalline cellulose pellet by using a fluidized bed, to achieve a drug-loaded pellet. An extended release coating solution consisting of cellulose acetate and polyethylene glycol was coated on the surface of the drug-loaded pellet, to obtain a desired different level of coating weight gain. The inlet airflow rate and the material temperature were adjusted to prevent spray drying of the coating solution or too wet pellets. The particle size of the prepared pellets was about 600 μm to about 1200 μm.

Figure 4:
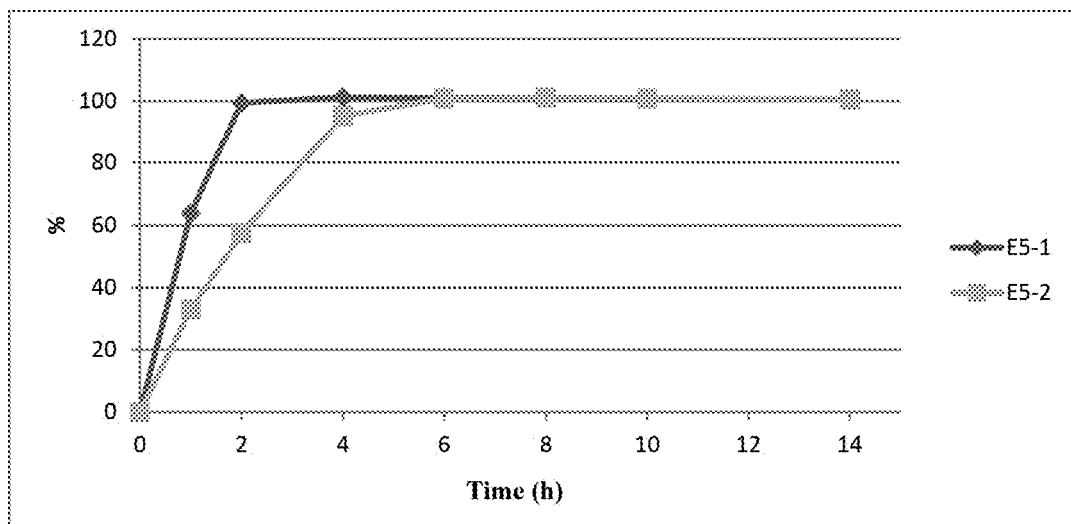
FIG. 4 illustrates the release characteristics of dissolution of the extended release multiparticulates of Example 5.
Figure 4:
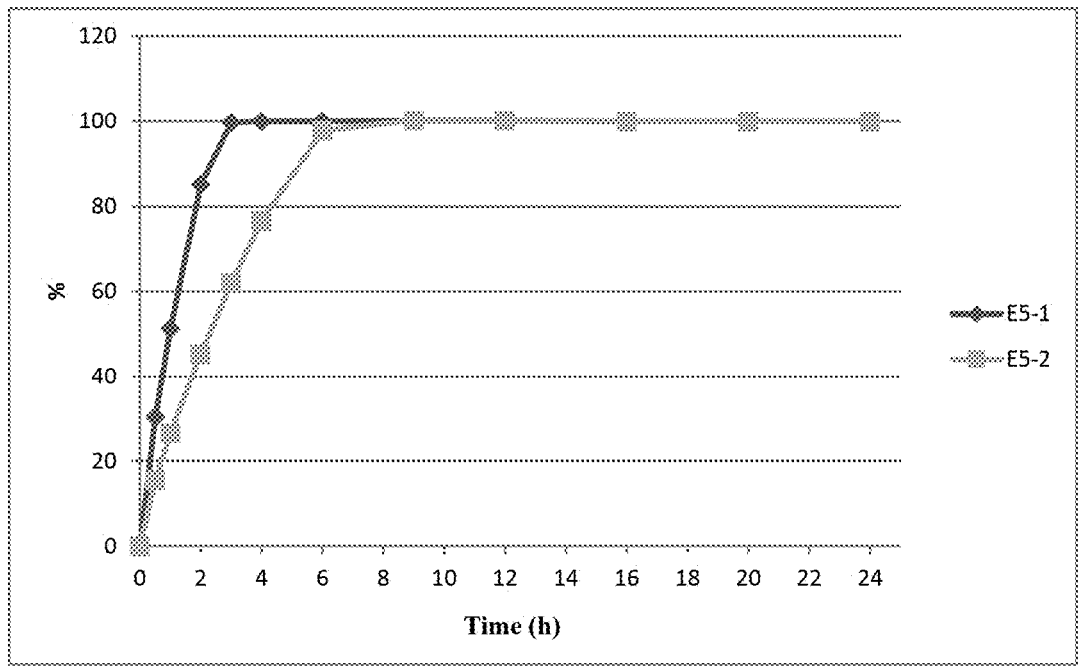

The in vitro dissolution was determined using a USP type 2 dissolution system (Paddle Apparatus) at 75 rpm and a temperature of 37±0.5° C. in a dissolution medium of 900 ml 0.1 N HCl. The dissolution samples were analyzed by high performance liquid chromatography (HPLC). The dissolution data of the two formulations in Example 5 are shown in table 8 and FIG. 4A.

TABLE 8

The dissolution data of the extended release multiparticulates of Example 5 (type 2 dissolution system).

| Time, hour | (%) | |
| --- | --- | --- |
| | E5-1 | E5-2 |
| 0 | 0.0 | 0.0 |
| 1 | 63.7 | 33.1 |
| 2 | 99.5 | 57.3 |
| 4 | 101.3 | 95.3 |
| 6 | 101.1 | 101.0 |
| 8 | 101.1 | 101.1 |
| 10 | 100.8 | 100.9 |
| 14 | 100.6 | 100.6 |

In Example 5, the dissolution was also determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for 18 hours. The dissolution samples were analyzed by high performance liquid chromatography (HPLC). The dissolution data are shown in table 9 and FIG. 4B.

TABLE 9

The dissolution data of the extended release multiparticulates of Example 5 (type 1 dissolution system).

| Time, hour | (%) | |
| --- | --- | --- |
| | E5-1 | E5-2 |
| 0 | 0.0 | 0.0 |
| 0.5 | 30.4 | 15.6 |
| 1 | 51.2 | 26.6 |
| 2 | 85.1 | 45.3 |
| 3 | 99.8 | 61.9 |
| 4 | 100.0 | 76.7 |
| 6 | 100.0 | 97.8 |
| 9 | 100.1 | 100.3 |
| 12 | 100.1 | 100.2 |
| 16 | 100.0 | 100.0 |
| 20 | 100.0 | 100.0 |
| 24 | 100.0 | 100.0 |

Example 6—Dosage Form of Extended Release Multiparticulates by Fluidized Bed Coating The formulations for preparing extended release multiparticulates by fluidized bed coating are shown in table 10.

TABLE 10

The formulations for preparing extended release multiparticulates by fluidized bed coating of Example 6.

| | | Formulation | | | |
|---|---|---|---|---|---|
| | | E6-1 | E6-2 | E6-3 | E6-4 |
| | | Batch number | | | |
| Composition | Ingredient (mg) | 20180823-1d(e)-1s-1f | 20180823-1d(e)-1s-2f | 20180823-1d(e)-1s-3f | 20180823-1d(e)-1s-4f |
| Drug-loaded core | Microcrystalline Cellulose Pellet | 50.19 | 50.19 | 50.19 | 50.19 |
| | Lacosamide | 200.00 | 200.00 | 200.00 | 200.00 |
| | Povidone | 20.00 | 20.00 | 20.00 | 20.00 |
| | Ethanol | —* | —* | —* | —* |
| Isolation layer | Opadry | 8.11 | 8.11 | 8.11 | 8.11 |
| | Purified Water | —* | —* | —* | —* |
| Extended release layer (RS:RL = 3:1) | Eudragit RS100 | 20.28 | 30.48 | 41.46 | 51.57 |
| | Eudragit RL100 | 6.76 | 10.16 | 13.82 | 17.19 |
| | Triethyl Citrate | 4.06 | 6.10 | 8.29 | 10.31 |
| | Talcum | 13.52 | 20.32 | 27.64 | 34.38 |
| | 95% Ethanol | —* | —* | —* | —* |

Note:
—* Solvent, evaporating during the process

A suspension of lacosamide and povidone was used as the drug coating solution, and the drug coating solution was uniformly coated on an inert microcrystalline cellulose pellet by using a fluidized bed, to achieve a desired drug loading level. An Opadry isolation layer was coated on the drug-loaded pellet, and then an extended release suspension consisting of Eudragit RS100/Eudragit RL100 (3:1), triethyl citrate, and talcum was coated on the surface of the drug-loaded pellet, to obtain a desired level of coating (e.g., 10%, 15%, 20%, 25%, w/w). The inlet airflow rate and the material temperature were adjusted to prevent spray drying of the coating solution or too wet pellets. The particle size of the prepared pellets was about 600 μm to 1200 μm.

Figure 5:
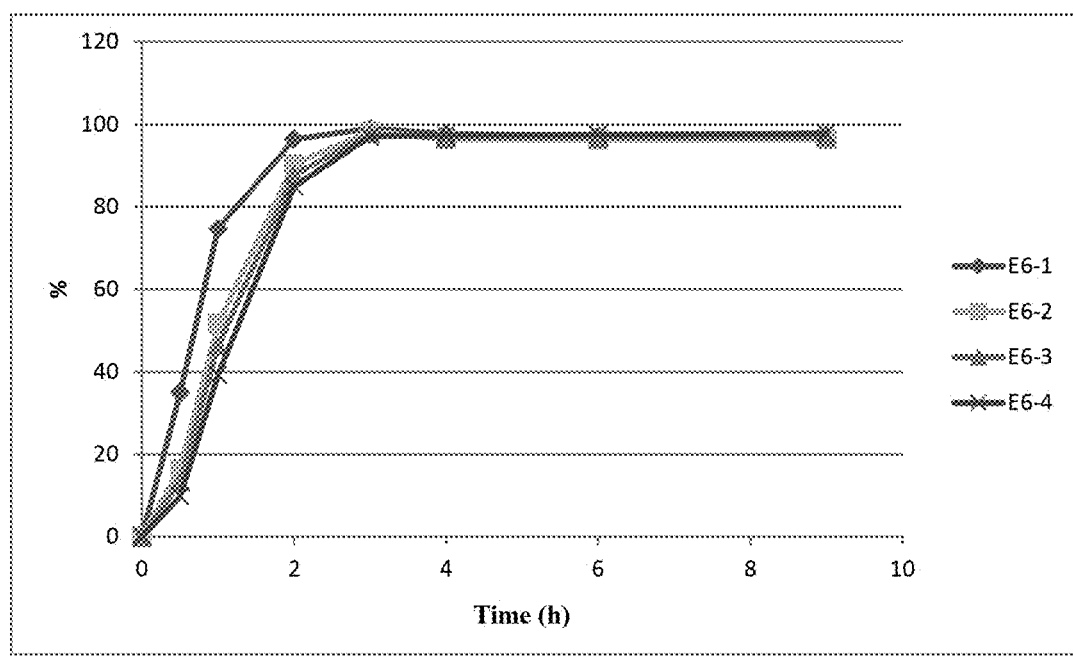
FIG. 5 illustrates the release characteristics of dissolution of the extended release multiparticulates of Example 6.

The dissolution was determined using a USP type 1 dissolution system (Basket Apparatus) at 100 rpm and a temperature of 37±0.5° C. in 900 ml of pH 1.0 buffer for 2 hours, then in 900 ml of pH 6.8 buffer using the same dissolution system, rotation speed and temperature for 4 hours, and then in 900 ml of pH 7.5 buffer using the same dissolution system, rotation speed and temperature for a period of time. The dissolution samples were analyzed by high performance liquid chromatography (HPLC). The dissolution data of lacosamide extended release multiparticulates of the four formulations in Example 6 are shown in table 11 and FIG. 5.

TABLE 11

The dissolution data of the extended release multiparticulates of Example 6.

| | (%) | | | |
|---|---|---|---|---|
| Time, hour | E6-1 | E6-2 | E6-3 | E6-4 |
| 0 | 0.0 | 0.0 | 0.0 | 0.0 |
| 0.5 | 34.9 | 16.6 | 13.2 | 9.8 |
| 1 | 74.8 | 51.7 | 46.3 | 39.3 |
| 2 | 96.4 | 90.4 | 87.8 | 84.9 |
| 3 | 99.0 | 98.3 | 97.7 | 97.1 |
| 4 | 97.7 | 96.4 | 96.8 | 97.4 |
| 6 | 97.2 | 96.3 | 96.8 | 97.5 |
| 9 | 97.2 | 96.4 | 97.0 | 97.8 |

Example 7—Dosage Form of Extended Release Multiparticulates by Fluidized Bed Coating The formulations for preparing extended release multiparticulates by fluidized bed coating are shown in table 12.

TABLE 12

The formulations for preparing extended release multiparticulates by fluidized bed coating of Example 7.

| | | Formulation | | | |
|---|---|---|---|---|---|
| | | E7-1 | E7-2 | E7-3 | E7-4 |
| | | Batch number | | | |
| Composition | Ingredient (mg) | 20180905-1d(e)-1s-1f | 20180905-1d(e)-1s-2f | 20180905-1d(e)-1s-3f | 20180905-1d(e)-1s-4f |
| Drug-loaded core | Microcrystalline Cellulose Pellet | 49.74 | 49.74 | 49.74 | 49.74 |
| | Lacosamide | 200.00 | 200.00 | 200.00 | 200.00 |
| | Povidone | 20.00 | 20.00 | 20.00 | 20.00 |
| | Ethanol | —* | —* | —* | —* |

TABLE 12-continued

The formulations for preparing extended release multiparticulates by fluidized bed coating of Example 7.

| Composition | Ingredient (mg) | Formulation E7-1 Batch number 20180905-1d(e)-1s-1f | E7-2 20180905-1d(e)-1s-2f | E7-3 20180905-1d(e)-1s-3f | E7-4 20180905-1d(e)-1s-4f |
|---|---|---|---|---|---|
| Isolation layer | Opadry | 8.90 | 8.90 | 8.90 | 8.90 |
|  | Purified Water | —* | —* | —* | —* |
| Extended release layer (RS:RL = 9:1) | Eudragit RS100 | 24.60 | 36.89 | 49.80 | 62.02 |
|  | Eudragit RL100 | 2.73 | 4.10 | 5.53 | 6.89 |
|  | Triethyl Citrate | 4.10 | 6.15 | 8.30 | 10.34 |
|  | Talcum | 13.67 | 20.49 | 27.67 | 34.45 |
|  | 95% Ethanol | —* | —* | —* | —* |

Note:
—* Solvent, evaporating during the process

The coating process is as described in Example 6.

Figure 6:
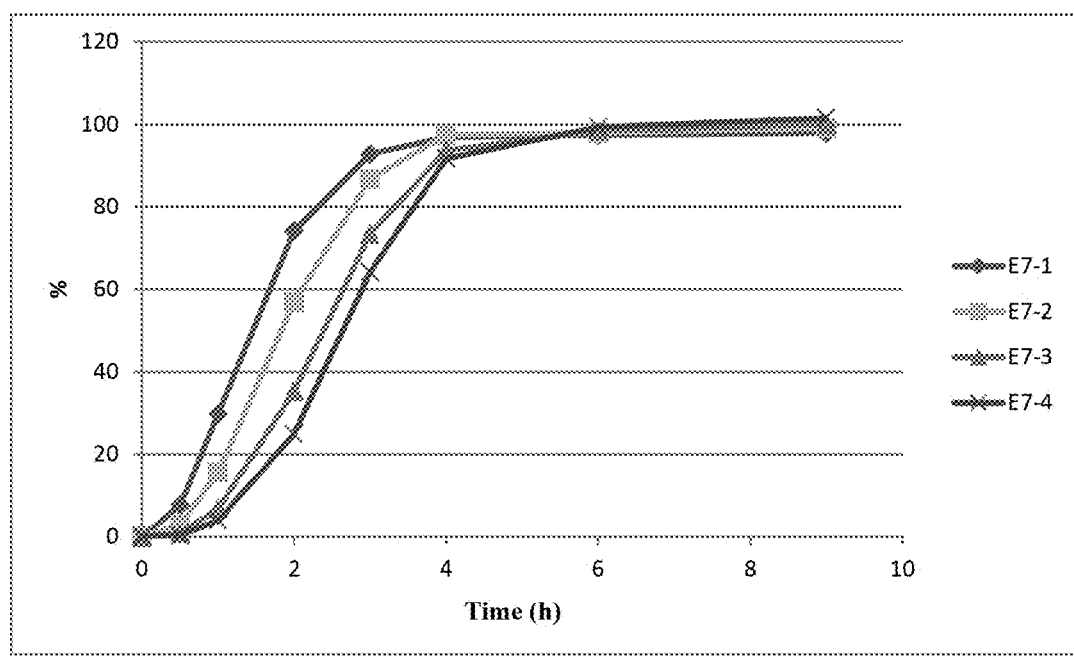
FIG. 6 illustrates the release characteristics of dissolution of the extended release multiparticulates of Example 7.

The dissolution was determined using a USP type 1 dissolution system (Basket Apparatus) at 100 rpm and a temperature of 37±0.5° C. in 900 ml of pH 1.0 buffer for 2 hours, then in 900 ml of pH 6.8 buffer using the same dissolution system, rotation speed and temperature for 4 hours, and then in 900 ml of pH 7.5 buffer using the same dissolution system, rotation speed and temperature for a period of time. The dissolution samples were analyzed by high performance liquid chromatography (HPLC). The dissolution data of lacosamide extended release multiparticulates of the four formulations in Example 7 are shown in table 13 and FIG. 6.

TABLE 13

The dissolution data of the extended release multiparticulates of Example 7.

| Time, hour | (%) E7-1 | E7-2 | E7-3 | E7-4 |
|---|---|---|---|---|
| 0 | 0.0 | 0.0 | 0.0 | 0.0 |
| 0.5 | 7.5 | 2.8 | 0.8 | 0.4 |
| 1 | 29.9 | 15.6 | 6.7 | 3.8 |
| 2 | 74.1 | 56.9 | 35.3 | 25.0 |
| 3 | 92.8 | 86.8 | 73.4 | 64.1 |
| 4 | 96.9 | 97.4 | 93.7 | 91.7 |
| 6 | 97.4 | 98.0 | 98.4 | 99.3 |
| 9 | 97.9 | 99.1 | 100.0 | 101.5 |

Example 8—Dosage Form of Extended Release Multiparticulates by Fluidized Bed Coating The formulations for preparing extended release multiparticulates by fluidized bed coating are shown in table 14.

TABLE 14

The formulations for preparing extended release multiparticulates by fluidized bed coating of Example 8.

| Ingredient (mg) | Formulation E8-1 Batch number 20181023-1d(e)-1s-1f-1s | E8-2 20181109-1d(e)-1s-1f-1s |
|---|---|---|
| Drug-loaded core | | |
| Lacosamide | 200.0 | 200.0 |
| Microcrystalline Cellulose Pellet | 50.0 | 50.0 |
| Povidone | 20.0 | 20.0 |
| Absolute Ethyl Alcohol* | —* | —* |
| Isolation layer | | |
| Opadry | 8.1 | 8.1 |
| Purified Water* | —* | —* |
| Extended release layer | | |
| Eudragit RS100 | 27.8 | 69.5 |
| Triethyl Citrate | 2.8 | 7.0 |
| Talcum | 13.9 | 34.8 |
| 95% Ethanol* | —* | —* |
| Protective layer | | |
| Opadry | 9.7 | 11.7 |
| Purified Water* | —* | —* |

Note:
—* Solvent, evaporating during the process

The coating process is as described in Example 6, except that a protective layer is further coated outside the extended release layer.

Figure 7:
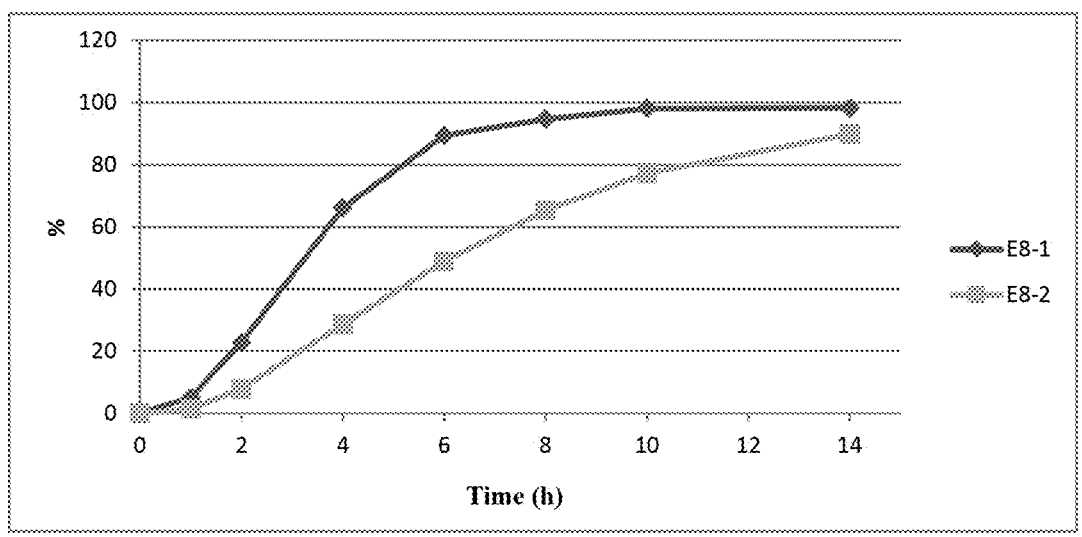
FIG. 7 illustrates the release characteristics of dissolution of the extended release multiparticulates of Example 8.

The in vitro dissolution was determined using a USP type 2 dissolution system (Paddle Apparatus) at 75 rpm and a temperature of 37±0.5° C. in a dissolution medium of 900 ml 0.1 N HCl. The dissolution samples were analyzed by high performance liquid chromatography (HPLC). The dissolution data of the two formulations in Example 8 are shown in table 15 and FIG. 7.

TABLE 15

The dissolution data of the extended release
multiparticulates of Example 8.

| Time, hour | (%) | |
|---|---|---|
| | E8-1 20181023-1d(e)-1s-1f-1s | E8-2 20181109-1d(e)-1s-1f-1s |
| 0 | 0 | 0 |
| 1 | 5.07 | 1.43 |
| 2 | 22.83 | 7.90 |
| 4 | 66.13 | 28.63 |
| 6 | 89.47 | 48.87 |
| 8 | 94.73 | 65.37 |
| 10 | 98.07 | 77.27 |
| 14 | 98.30 | 89.93 |

Example 9—Dosage Form of Lacosamide Extended Release Capsules by Fluidized Bed Coating The formulations for preparing extended release multiparticulates of lacosamide extended release capsules by fluidized bed coating are shown in table 16.

TABLE 16

The formulations for preparing extended release
multiparticulates of lacosamide extended release
capsules by fluidized bed coating of Example 9.

| | Formulation (mg) | | |
|---|---|---|---|
| | E9-1 | E9-2 | E9-3 |
| Drug-loaded core | | | |
| Lacosamide | 200.0 | 200.0 | 200.0 |
| Microcrystalline Cellulose Pellet | 50.0 | 50.0 | 50.0 |
| Povidone | 20.0 | 20.0 | 20.0 |
| Absolute Ethyl Alcohol* | —* | —* | —* |
| Isolation layer | | | |
| Opadry | 8.1 | 8.1 | 8.1 |
| Purified Water* | —* | —* | —* |
| Extended release layer | | | |
| Eudragit RS100 | 19.5 | 41.7 | 55.6 |
| Triethyl Citrate | 1.9 | 4.2 | 5.6 |
| Talcum | 9.7 | 20.9 | 27.8 |
| 95% Ethanol* | —* | —* | —* |
| Protective layer | | | |
| Opadry | 9.3 | 10.3 | 11.0 |
| Purified Water* | —* | —* | —* |

Note:
—* Solvent, evaporating during the process

The coating process is as described in Example 8, and the resulting extended release multiparticulates were filled into a size 0 capsule by a capsule filling machine.

The in vitro dissolution of the capsule was determined using a USP type 1 dissolution system (Basket Apparatus) at 100 rpm and a temperature of 37±0.5° C. in 900 ml of pH 1.0 HCl/34 mM NaCl buffer for 2 hours, then in 900 ml of pH 6.8 phosphate/100 mM NaCl buffer using the same dissolution system, rotation speed and temperature for 4 hours, and then in 900 ml of pH 7.5 phosphate/100 mM NaCl buffer using the same dissolution system, rotation speed and temperature for 18 hours. The dissolution samples were analyzed by high performance liquid chromatography (HPLC). The dissolution data of the lacosamide extended release capsules of the three formulations in Example 9 are shown in table 17.

TABLE 17

The dissolution data of the lacosamide
extended release capsules of Example 9.

| | (%) | | |
|---|---|---|---|
| Time, hour | E9-1 | E9-2 | E9-3 |
| 0 | 0.0 | 0.0 | 0.0 |
| 1 | 1.0 | 0.0 | 0.0 |
| 2 | 6.0 | 0.0 | 0.0 |
| 3 | 17.3 | 0.7 | 0.0 |
| 4 | 36.3 | 3.8 | 0.0 |
| 5 | 54.8 | 11.7 | 1.5 |
| 6 | 69.3 | 25.0 | 5.7 |
| 8 | 84.8 | 61.7 | 21.8 |
| 10 | 92.5 | 88.0 | 50.2 |
| 12 | 97.7 | 95.5 | 81.0 |
| 16 | 102.0 | 99.8 | 100.7 |
| 20 | 102.3 | 100.7 | 102.2 |
| 24 | 102.3 | 100.8 | 102.5 |

Example 10—Dosage Form of Lacosamide Extended Release Capsules by Fluidized Bed Coating The formulations for preparing extended release multiparticulates of lacosamide extended release capsules by fluidized bed coating are shown in table 18.

TABLE 18

The formulations for preparing extended release
multiparticulates of lacosamide extended release
capsules by fluidized bed coating of Example 10.

| | Batch number (Formulation) | | |
|---|---|---|---|
| Ingredient (mg) | 20190228-1d(e)-1s-1f(b) (Formulation 1 (F1)) | 20190228-1d(e)-1s-1f(f) (Formulation 2 (F2)) | 20190228-1d(e)-1s-1f(h)-1s (Formulation 3 (F3)) |
| Drug-loaded core | | | |
| Lacosamide | 200.0 | 200.0 | 200.0 |
| Microcrystalline Cellulose Pellet | 50.0 | 50.0 | 50.0 |
| Povidone | 20.0 | 20.0 | 20.0 |
| Absolute Ethyl Alcohol* | —* | —* | —* |
| Isolation layer | | | |
| Opadry | 8.1 | 8.1 | 8.1 |
| Purified Water* | —* | —* | —* |
| Extended release layer | | | |
| Eudragit RS100 | 27.8 | 55.6 | 69.5 |
| Triethyl Citrate | 2.8 | 5.6 | 7.0 |
| Talcum | 13.9 | 27.8 | 34.8 |
| 95% Ethanol* | —* | —* | —* |
| Protective layer | | | |
| Opadry | / | / | 11.7 |
| Purified Water* | / | / | —* |

Note:
—* Solvent, evaporating during the process

The coating process is as described in Example 8, and the resulting extended release multiparticulates were filled into a capsule of a suitable size (e.g., size 0, size 1 and size 4 capsules) by a capsule filling machine.

Figure 8:
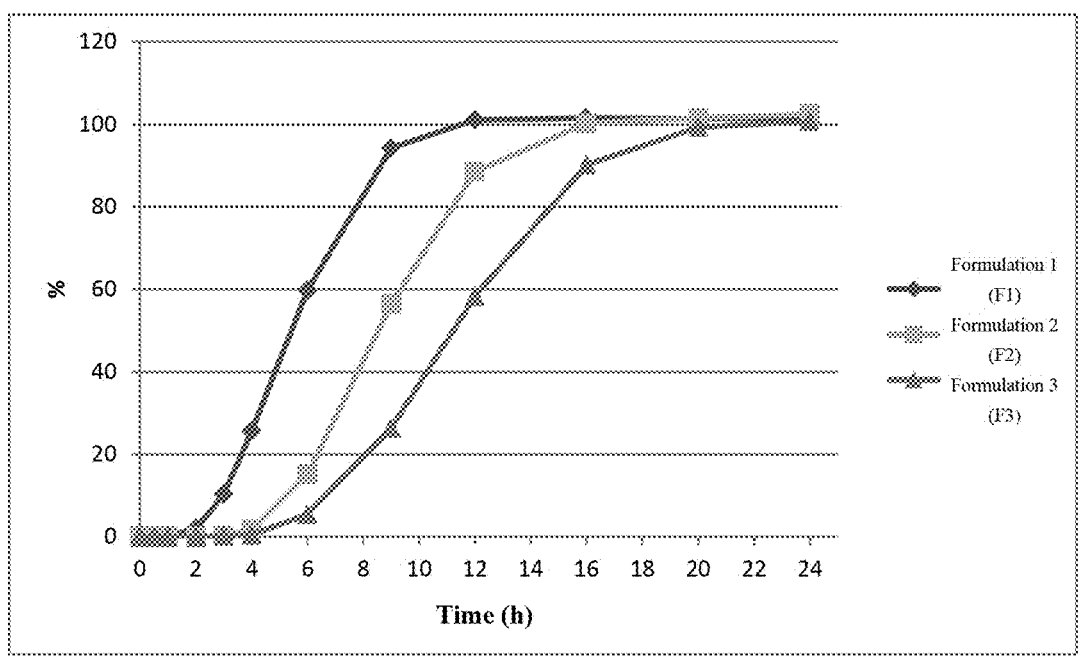
FIG. 8 illustrates the release characteristics of dissolution of the extended release capsule of lacosamide of Example 10.

The in vitro dissolution was determined using a USP type 1 dissolution system (Basket Apparatus) at 100 rpm and a temperature of 37±0.5° C. in 900 ml of pH 1.0 HCl/NaCl buffer for 2 hours, then in 900 ml of pH 6.8 phosphate/NaCl buffer using the same dissolution system, rotation speed and temperature for 4 hours, and then in 900 ml of pH 7.5 phosphate/NaCl buffer using the same dissolution system, rotation speed and temperature for 18 hours. The dissolution samples were analyzed by high performance liquid chromatography (HPLC). The dissolution data of the lacosamide extended release capsules of the three formulations in Example 10 are shown in table 19 and FIG. 8. The use of Eudragit RS100 coating resulted in release characteristics of in vitro dissolution similar to those resulting from the use of pH dependent polymer coatings, e.g., delayed release for 1 hour, 3 hours or 5 hours in a medium of pH 1.0 or pH 1.0 to pH 6.8. Compared with the release characteristics of ordinary extended release dosage forms, this release characteristic can reduce or avoid the risk of in vivo burst release of the drug from the extended release dosage forms.

Example 11—Dosage Form of Extended Release Multiparticulates by Fluidized Bed Coating The formulations for preparing extended release multiparticulates by fluidized bed coating are shown in table 20.

TABLE 20

The formulations for preparing extended release multiparticulates by fluidized bed coating of Example 11.

| Composition | | Formulation (mg) | | | | | |
|---|---|---|---|---|---|---|---|
| | | E11-1 | E11-2 | E11-3 | E11-4 | E11-5 | E11-6 |
| Drug-loaded core | Microcrystalline Cellulose Pellet | 50.35 | 50.35 | 50.35 | 50.35 | 50.35 | 50.35 |
| | Lacosamide | 200.00 | 200.00 | 200.00 | 200.00 | 200.00 | 200.00 |
| | Povidone | 20.00 | 20.00 | 20.00 | 20.00 | 20.00 | 20.00 |
| | Ethanol | —* | —* | —* | —* | —* | —* |
| Isolation layer | Opadry | 8.1.6 | 8.16 | 8.16 | 8.16 | 8.16 | 8.16 |
| | Purified Water | —* | —* | —* | —* | —* | —* |
| Extended release layer | Ethyl Cellulose | 17.04 | 22.50 | 28.21 | 33.73 | 39.60 | 45.01 |
| | Hydroxypropyl Methyl Cellulose | 9.59 | 12.66 | 15.87 | 18.97 | 22.28 | 25.32 |
| | Triethyl Citrate | 3.20 | 4.23 | 5.30 | 6.34 | 7.45 | 8.46 |
| | 90% Ethanol | —* | —* | —* | —* | —* | —* |

Note:
—* Solvent, evaporating during the process

A suspension of lacosamide and povidone was used as the drug coating solution, and the drug coating solution was uniformly coated on an inert microcrystalline cellulose pellet by using a fluidized bed, to achieve a desired drug loading level. An Opadry isolation layer was coated on the drug-loaded pellet, and then an extended release coating solution consisting of ethyl cellulose, hydroxypropyl methyl cellulose and triethyl citrate was coated on the surface of the drug-loaded pellet, to obtain a desired different level of coating weight gain. The inlet airflow rate and the material temperature were adjusted to prevent spray drying of the coating solution or too wet pellets. The particle size of the prepared pellets was about 600 μm to about 1200 μm.

The in vitro dissolution was determined using a USP type 1 dissolution system (Basket Apparatus) at 100 rpm and a temperature of 37±0.5° C. in a dissolution medium of pH 6.8 phosphate buffer. The dissolution samples were analyzed by high performance liquid chromatography (HPLC). The dissolution data of the six formulations in Example 11 are shown in table 21.

TABLE 19

The dissolution data of the lacosamide extended release capsules of Example 10.

| | (%) | | |
|---|---|---|---|
| Time, hour | Formulation 1 (F1) | Formulation 2 (F2) | Formulation 3 (F3) |
| 0 | 0.0 | 0.0 | 0.0 |
| 0.5 | 0.0 | 0.0 | 0.0 |
| 1 | 0.1 | 0.0 | 0.0 |
| 2 | 1.9 | 0.0 | 0.0 |
| 3 | 10.2 | 0.2 | 0.1 |
| 4 | 25.6 | 1.7 | 0.4 |
| 6 | 59.8 | 15.2 | 5.4 |
| 9 | 94.3 | 56.4 | 26.4 |
| 12 | 101.1 | 88.6 | 58.3 |
| 16 | 101.5 | 100.3 | 90.2 |
| 20 | 101.4 | 101.5 | 99.3 |
| 24 | 101.6 | 102.4 | 100.7 |

TABLE 21

The dissolution data of the extended release multiparticulates of Example 11.

| | (%) | | | | | |
|---|---|---|---|---|---|---|
| Time, hour | E11-1 | E11-2 | E11-3 | E11-4 | E11-5 | E11-6 |
| 0 | 0.0 | 0.0 | 0.0 | 0.0 | 0.0 | 0.0 |
| 0.5 | 2.5 | 1.3 | 0.9 | 0.5 | 0.3 | 0.2 |
| 1 | 8.3 | 4.9 | 3.5 | 2.2 | 1.6 | 1.2 |
| 2 | 22.7 | 15.0 | 11.2 | 7.5 | 5.8 | 4.6 |
| 3 | 38.5 | 26.7 | 20.2 | 14.0 | 11.0 | 8.8 |
| 4 | 54.2 | 39.0 | 30.0 | 21.2 | 16.8 | 13.5 |
| 6 | 82.0 | 63.0 | 50.2 | 36.7 | 29.6 | 24.1 |
| 9 | 97.2 | 90.0 | 78.3 | 61.3 | 50.5 | 41.8 |
| 12 | 98.9 | 98.2 | 94.7 | 82.9 | 71.3 | 60.3 |

Example 12—Dosage Form of Extended Release Multiparticulates by Fluidized Bed Coating The formulations for preparing extended release multiparticulates by fluidized bed coating are shown in table 22.

TABLE 22

The formulations for preparing extended release multiparticulates by fluidized bed coating of Example 12.

| Composition | | Formulation (mg) | | | | | |
|---|---|---|---|---|---|---|---|
| | | E12-1 | E12-2 | E12-3 | E12-4 | E12-5 | E12-6 |
| Drug-loaded core | Microcrystalline Cellulose Pellet | 50.35 | 50.35 | 50.35 | 50.35 | 50.35 | 50.35 |
| | Lacosamide | 200.00 | 200.00 | 200.00 | 200.00 | 200.00 | 200.00 |
| | Povidone | 20.00 | 20.00 | 20.00 | 20.00 | 20.00 | 20.00 |
| | Ethanol | —* | —* | —* | —* | —* | —* |
| Isolation layer | Opadry | 8.06 | 8.06 | 8.06 | 8.06 | 8.06 | 8.06 |
| | Purified Water | —* | —* | —* | —* | —* | —* |
| Extended release layer | Ethyl Cellulose | 22.77 | 28.23 | 33.80 | 39.26 | 44.52 | 50.39 |
| | Hydroxypropyl Methyl Cellulose | 14.23 | 17.64 | 21.12 | 24.53 | 27.82 | 31.50 |
| | Triethyl Citrate | 4.28 | 5.31 | 6.35 | 7.38 | 8.37 | 9.47 |
| | 90% Ethanol | —* | —* | —* | —* | —* | —* |

Note:
—* Solvent, evaporating during the process

A suspension of lacosamide and povidone was used as the drug coating solution, and the drug coating solution was uniformly coated on an inert microcrystalline cellulose pellet by using a fluidized bed, to achieve a desired drug loading level. An Opadry isolation layer was coated on the drug-loaded pellet, and then an extended release coating solution consisting of ethyl cellulose, hydroxypropyl methyl cellulose and triethyl citrate was coated on the surface of the drug-loaded pellet, to obtain a desired different level of coating weight gain. The inlet airflow rate and the material temperature were adjusted to prevent spray drying of the coating solution or too wet pellets. The particle size of the prepared pellets was about 600 μm to about 1200 μm.

The in vitro dissolution was determined using a USP type 1 dissolution system (Basket Apparatus) at 100 rpm and a temperature of 37±0.5° C. in a dissolution medium of pH 6.8 phosphate buffer. The dissolution samples were analyzed by high performance liquid chromatography (HPLC). The dissolution data of the six formulations in Example 12 are shown in table 23.

TABLE 23

The dissolution data of the extended release multiparticulates of Example 12.

| | (%) | | | | | |
|---|---|---|---|---|---|---|
| Time, hour | E12-1 | E12-2 | E12-3 | E12-4 | E12-5 | E12-6 |
| 0 | 0.0 | 0.0 | 0.0 | 0.0 | 0.0 | 0.0 |
| 0.5 | 6.1 | 3.7 | 2.6 | 1.9 | 1.4 | 1.1 |
| 1 | 18.3 | 11.9 | 8.6 | 6.7 | 5.5 | 4.4 |
| 2 | 47.4 | 33.0 | 24.6 | 19.6 | 16.5 | 13.9 |
| 3 | 76.3 | 55.9 | 42.9 | 34.9 | 29.8 | 25.3 |
| 4 | 93.3 | 77.1 | 61.8 | 51.3 | 44.5 | 38.1 |
| 6 | 97.6 | 96.2 | 89.7 | 81.6 | 73.3 | 64.9 |
| 9 | 97.2 | 96.7 | 95.3 | 96.0 | 94.8 | 92.0 |
| 12 | 97.0 | 96.4 | 95.3 | 96.4 | 96.4 | 96.1 |

Example 13—Dosage Form of Extended Release Multiparticulates by Fluidized Bed Coating The formulations for preparing extended release multiparticulates by fluidized bed coating are shown in table 24.

TABLE 24

The formulations for preparing extended release multiparticulates by fluidized bed coating of Example 13.

| Composition | | Formulation (mg) | | | | | | |
|---|---|---|---|---|---|---|---|---|
| | | E13-1 | E13-2 | E13-3 | E13-4 | E13-5 | E13-6 | E13-7 |
| Drug-loaded core | Microcrystalline Cellulose Pellet | 50.35 | 50.35 | 50.35 | 50.35 | 50.35 | 50.35 | 50.35 |
| | Lacosamide | 200.00 | 200.00 | 200.00 | 200.00 | 200.00 | 200.00 | 200.00 |
| | Povidone | 20.00 | 20.00 | 20.00 | 20.00 | 20.00 | 20.00 | 20.00 |
| | Ethanol | —* | —* | —* | —* | —* | —* | —* |
| Isolation layer | Opadry | 8.10 | 8.10 | 8.10 | 8.10 | 8.10 | 8.10 | 8.10 |
| | Purified Water | —* | —* | —* | —* | —* | —* | —* |

TABLE 24-continued

The formulations for preparing extended release multiparticulates by fluidized bed coating of Example 13.

| Composition | | Formulation (mg) | | | | | | |
|---|---|---|---|---|---|---|---|---|
| | | E13-1 | E13-2 | E13-3 | E13-4 | E13-5 | E13-6 | E13-7 |
| Extended release layer | Ethyl Cellulose | 17.44 | 22.67 | 28.45 | 33.96 | 39.71 | 45.14 | 50.56 |
| | Hydroxypropyl Methyl Cellulose | 11.99 | 15.58 | 19.56 | 23.34 | 27.30 | 31.03 | 34.76 |
| | Triethyl Citrate | 3.28 | 4.26 | 5.35 | 6.38 | 7.47 | 8.49 | 9.51 |
| | 90% Ethanol | —* | —* | —* | —* | —* | —* | —* |

Note:
—* Solvent, evaporating during the process

A suspension of lacosamide and povidone was used as the drug coating solution, and the drug coating solution was uniformly coated on an inert microcrystalline cellulose pellet by using a fluidized bed, to achieve a desired drug loading level. An Opadry isolation layer was coated on the drug-loaded pellet, and then an extended release coating solution consisting of ethyl cellulose, hydroxypropyl methyl cellulose and triethyl citrate was coated on the surface of the drug-loaded pellet, to obtain a desired different level of coating weight gain. The inlet airflow rate and the material temperature were adjusted to prevent spray drying of the coating solution or too wet pellets. The particle size of the prepared pellets was about 600 μm to about 1200 μm.

The in vitro dissolution was determined using a USP type 1 dissolution system (Basket Apparatus) at 100 rpm and a temperature of 37±0.5° C. in a dissolution medium of pH 6.8 phosphate buffer. The dissolution samples were analyzed by high performance liquid chromatography (HPLC). The dissolution data of the seven formulations in Example 13 are shown in table 25.

TABLE 25

The dissolution data of the extended release multiparticulates of Example 13.

| Time, hour | (%) | | | | | | |
|---|---|---|---|---|---|---|---|
| | E13-1 | E13-2 | E13-3 | E13-4 | E13-5 | E13-6 | E13-7 |
| 0 | 0.0 | 0.0 | 0.0 | 0.0 | 0.0 | 0.0 | 0.0 |
| 0.5 | 21.0 | 15.4 | 9.7 | 7.1 | 5.8 | 4.2 | 3.6 |
| 1 | 53.8 | 39.0 | 26.8 | 20.7 | 16.9 | 13.1 | 11.7 |
| 2 | 94.8 | 85.1 | 67.0 | 54.6 | 45.1 | 36.4 | 33.3 |
| 3 | 97.1 | 97.5 | 94.2 | 86.3 | 75.2 | 63.5 | 58.6 |
| 4 | 97.5 | 98.2 | 98.0 | 97.8 | 92.9 | 86.3 | 81.6 |
| 6 | 97.7 | 98.6 | 98.2 | 98.8 | 97.3 | 97.2 | 97.1 |
| 9 | 98.2 | 98.6 | 98.4 | 99.4 | 97.7 | 97.7 | 98.1 |
| 12 | 98.4 | 99.1 | 98.6 | 99.5 | 97.9 | 98.0 | 98.2 |

Example 14—Dosage Form of a Lacosamide Extended Release Dosage Form by Fluidized Bed Coating The formulations for preparing a combination comprising an extended release portion and an immediate release portion (an immediate release layer or immediate release multiparticulates) by fluidized bed coating are shown in table 26.

TABLE 26

The formulations for preparing a lacosamide extended release dosage form by fluidized bed coating of Example 14.

| Composition | | | Formulation (mg) | | | |
|---|---|---|---|---|---|---|
| | | | | | E14-3 | |
| | | | E14-1 | E14-2 | Extended release pellet | Immediate release pellet |
| Drug-loaded core | Microcrystalline Cellulose Pellet | | 50.35 | 45.32 | 45.32 | 5.04 |
| | Lacosamide | | 200.00 | 180.00 | 180.00 | 20.00 |
| | Povidone | | 20.00 | 18.00 | 18.00 | 2.00 |
| | Ethanol | | —* | —* | —* | —* |
| Isolation layer | Opadry | | 8.08 | 7.27 | 7.27 | 0.81 |
| | Purified Water | | —* | —* | —* | —* |

TABLE 26-continued

The formulations for preparing a lacosamide extended release dosage form by fluidized bed coating of Example 14.

| | | Formulation (mg) | | | |
|---|---|---|---|---|---|
| | | | | E14-3 | |
| Composition | | E14-1 | E14-2 | Extended release pellet | Immediate release pellet |
| Extended release layer | Ethyl Cellulose | 22.14 | 19.93 | 19.93 | / |
| | Hydroxypropyl Methyl Cellulose | 12.45 | 11.21 | 11.21 | |
| | Triethyl Citrate | 4.16 | 3.74 | 3.74 | |
| | 90% Ethanol | —* | —* | —* | |
| Isolation layer | Opadry | 11.60 | 10.44 | 10.44 | / |
| | Purified Water | —* | —* | —* | |
| Drug layer (immediate release layer) | Lacosamide | / | 20.80 | / | / |
| | Povidone | | 2.08 | | |
| | Ethanol | | —* | | |
| Protective layer | Opadry | / | 9.78 | / | / |
| | Purified Water | | —* | | |

Note:
—* Solvent, evaporating during the process

A suspension of lacosamide and povidone was used as the drug coating solution, and the drug coating solution was uniformly coated on an inert microcrystalline cellulose pellet by using a fluidized bed, to achieve a desired drug loading level. An Opadry isolation layer was coated on the drug-loaded pellet, to obtain the immediate release pellet, and the particle size of the prepared immediate release pellets was about 600 μm to about 1000 μm. An extended release coating solution consisting of ethyl cellulose, hydroxypropyl methyl cellulose and triethyl citrate was coated on the surface of the immediate release pellet, then an Opadry isolation layer was coated thereon, and the extended release pellet can be obtained, and the particle size of the prepared extended release pellets was about 600 μm to about 1200 μm.

A part of extended release pellets were selected, and a suspension of lacosamide and povidone was used as the drug coating solution, which was coated on the extended release pellet to achieve a desired drug loading level, then an Opadry isolation layer was coated thereon, and the pellets containing both immediate release and extended release portions were filled into a capsule shell (E14-2).

For formulation E14-3, both the above-mentioned extended release and immediate release pellets were mixed uniformly in the given proportion and filled into capsules.

The in vitro dissolution was determined using a USP type 1 dissolution system (Basket Apparatus) at 100 rpm and a temperature of 37±0.5° C. in a dissolution medium of pH 6.8 phosphate buffer. The dissolution samples were analyzed by high performance liquid chromatography (HPLC). The dissolution data of the three formulations in Example 14 are shown in table 27.

TABLE 27

The dissolution data of the extended release dosage forms of Example 14.

| | (%) | | |
|---|---|---|---|
| Time, hour | E14-1 | E14-2 | E14-3 |
| 0 | 0.0 | 0.0 | 0.0 |
| 0.5 | 2.5 | 13.1 | 12.5 |
| 1 | 10.6 | 22.8 | 20.2 |
| 2 | 32.5 | 46.6 | 40.1 |
| 3 | 57.1 | 71.6 | 62.7 |
| 4 | 79.0 | 90.1 | 82.3 |
| 6 | 97.1 | 98.6 | 98.4 |
| 9 | 98.3 | 98.9 | 99.6 |
| 12 | 98.5 | 99.0 | 99.7 |

Example 15—Dosage Form of Extended Release Multiparticulates by Fluidized Bed Coating The formulations for preparing extended release multiparticulates by fluidized bed coating are shown in table 28.

TABLE 28

The formulations for preparing extended release multiparticulates by fluidized bed coating of Example 15.

| Composition | | Formulation (mg) | | | | | | | |
|---|---|---|---|---|---|---|---|---|---|
| | | E15-0 | E15-1 | E15-2 | E15-3 | E15-4 | E15-5 | E15-6 | E15-7 |
| Drug-loaded core | Microcrystalline Cellulose Pellet | 50.0 | 50.0 | 50.0 | 50.0 | 50.0 | 50.0 | 50.0 | 50.0 |
| | Lacosamide | 200.0 | 200.0 | 200.0 | 200.0 | 200.0 | 200.0 | 200.0 | 200.0 |
| | Povidone | 20.0 | 20.0 | 20.0 | 20.0 | 20.0 | 20.0 | 20.0 | 20.0 |
| | Ethanol | —* | —* | —* | —* | —* | —* | —* | —* |
| Isolation layer | Opadry | 8.1 | 8.1 | 8.1 | 8.1 | 8.1 | 8.1 | 8.1 | 8.1 |
| | Purified Water | —* | —* | —* | —* | —* | —* | —* | —* |
| Extended release layer | Ethyl Cellulose | / | 16.7 | 27.8 | 33.4 | 38.9 | 44.5 | 50.1 | 83.4 |
| | Hydroxypropyl Methyl Cellulose | / | 9.39 | 15.64 | 18.77 | 21.90 | 25.03 | 28.16 | 46.93 |
| | Tri ethyl Citrate | / | 3.14 | 5.23 | 6.27 | 7.32 | 8.37 | 9.41 | 15.68 |
| | 90% Ethanol | / | —* | —* | —* | —* | —* | —* | —* |

Glatt GPCG-60 was used for scale-up production of 51.6 kg/batch. A suspension of lacosamide and povidone was used as the drug coating solution, and the drug coating solution was uniformly coated on an inert microcrystalline cellulose pellet, to achieve a desired drug loading level. An Opadry isolation layer was coated on the drug-loaded pellet, and then an extended release coating solution consisting of ethyl cellulose, hydroxypropyl methyl cellulose and triethyl citrate was coated on the surface of the drug-loaded pellet, to obtain desired different levels of extended release coating weight gain. The particle size of the prepared pellets was about 600 μm to about 1200 μm.

The prepared extended release pellets and immediate release pellets were filled into capsules at a ratio of 9:1 according to the active ingredient lacosamide.

Example 16—Simulation of Steady-State Pharmacokinetic Parameters

Designs were made for in vitro release profiles of three extended release (ER) formulations (F1, F2, and F3 described in Example 10), and their in vivo absorption profiles were predicted. This example also includes combinations of the above three formulations and an immediate release (IR) portion in different proportions. Based on the single dose pharmacokinetic parameters of Vimpat® IR tablets, the steady-state $AUC_{ss}$, $C_{ss,max}$ and $C_{ss,min}$ of these formulations were simulated and predicted by using the pharmacokinetic software Gastroplus. The simulation results are shown in table 29.

TABLE 29

Simulation of steady-state pharmacokinetic parameters.

| Formulation | Dose (mg) | $T_{max, ss}$ (h) | $C_{max, ss}$ (ug/mL) | $C_{min, ss}$ (ug/mL) | $AUC_{ss}$ (h*ug/mL) | PTF (%) |
|---|---|---|---|---|---|---|
| IR, Vimpat ® | 200 b.i.d | 0.76 | 11.64 | 6.09 | 102.7 | 64.9 |
| ER, F1 | 400 q.d | 10.02 | 10.41 | 5.93 | 204.4 | 52.6 |
| ER, F2 | 400 q.d | 13.91 | 10.68 | 6.95 | 215.0 | 41.6 |
| ER, F3 | 400 q.d | 14.05 | 9.57 | 6.69 | 200.1 | 34.5 |
| F2*90% + IR*10% | 400 q.d | 13.77 | 10.32 | 7.54 | 214.0 | 31.2 |
| F2*80% + IR*20% | 400 q.d | 13.19 | 9.98 | 7.2 | 213.1 | 31.3 |
| F2*70% + IR*30% | 400 q.d | 0.79 | 10.03 | 6.85 | 212.1 | 36.0 |
| F2*60% + IR*40% | 400 q.d | 0.79 | 10.85 | 6.51 | 211.1 | 49.3 |

In addition, designs were made for in vitro release profiles of two extended release (ER) formulations (E11-1 and E11-4 described in Example 11), and their in vivo absorption profiles were predicted. This example also includes combinations of the above two formulations and an immediate release (IR) portion in different proportions. Based on the single dose pharmacokinetic parameters of Vimpat® IR tablets, the steady-state $AUC_{ss}$, $C_{ss,max}$ and $C_{ss,min}$ of these formulations were simulated and predicted by using the pharmacokinetic software Gastroplus. The simulation results are shown in table 30. The PTF can be further reduced by introducing a certain proportion of the immediate release portion into the lacosamide extended release multiparticulates.

TABLE 30

Simulation of steady-state pharmacokinetic parameters.

| Formulation | Dose (mg) | $T_{max, ss}$ (h) | $C_{max, ss}$ (ug/mL) | $C_{min, ss}$ (ug/mL) | $AUC_{ss}$ (h*ug/mL) | PTF (%) |
|---|---|---|---|---|---|---|
| IR, Vimpat ® | 200 b.i.d | 0.76 | 11.64 | 6.09 | 102.7 | 64.9 |
| E11-1 | 400 q.d | 11.89 | 10.68 | 6.72 | 215.1 | 44.2 |
| E11-4 | 400 q.d | 11.60 | 9.57 | 6.61 | 200.0 | 35.5 |
| E11-1*90% + IR*10% | 400 q.d | 11.03 | 10.4 | 6.93 | 214.2 | 38.9 |
| E11-1*80% + IR*20% | 400 q.d | 10.88 | 10.19 | 6.65 | 213.4 | 39.8 |
| E11-1*70% + IR*30% | 400 q.d | 10.88 | 9.99 | 6.38 | 212.5 | 40.8 |
| E11-1*60% + IR*40% | 400 q.d | 0.50 | 10.58 | 6.1 | 211.7 | 50.8 |
| E11-4*90% + IR*10% | 400 q.d | 11.46 | 9.37 | 6.73 | 199.0 | 31.8 |
| E11-4*80% + IR*20% | 400 q.d | 11.03 | 9.18 | 6.47 | 198.0 | 32.8 |
| E11-4*70% + IR*30% | 400 q.d | 10.02 | 9.04 | 6.2 | 197.0 | 34.6 |
| E11-4*60% + IR*40% | 400 q.d | 0.94 | 9.3 | 5.94 | 196.0 | 41.1 |

Example 17—Bioavailability Study

Figure 9:
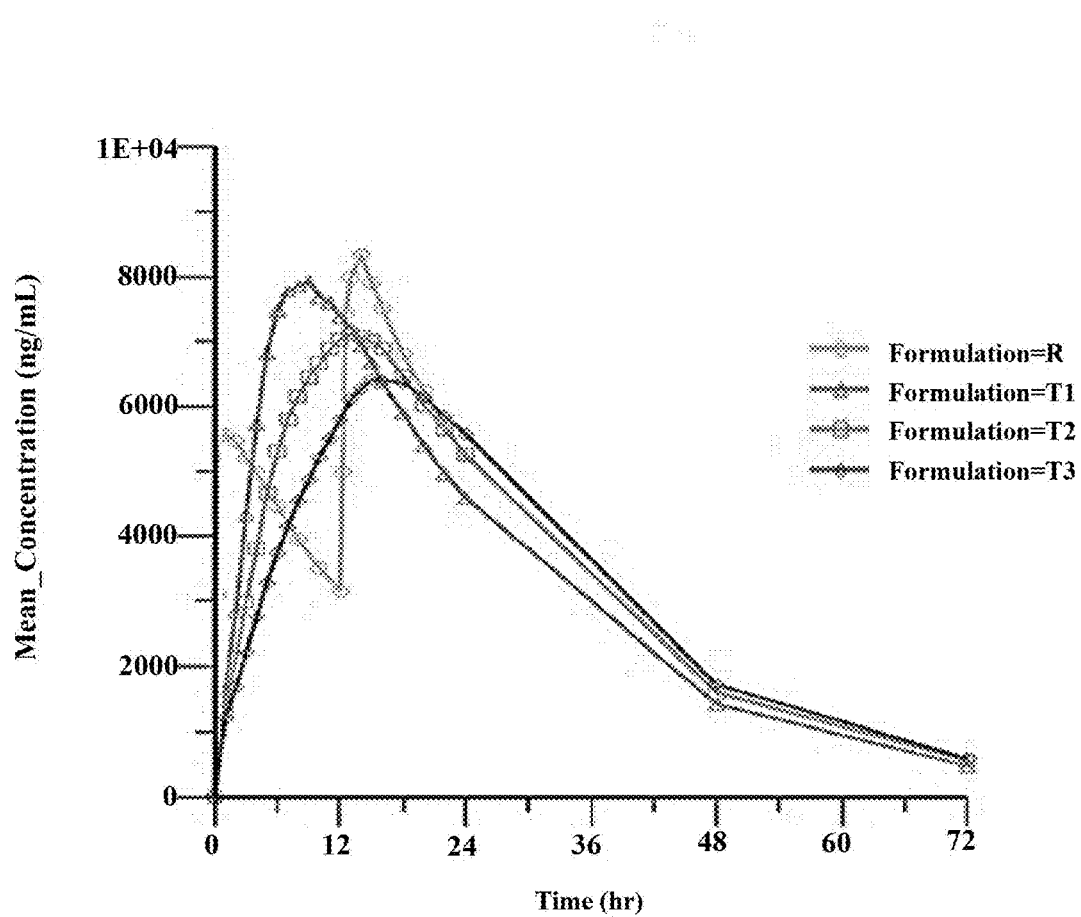
FIG. 9 illustrates the single dose pharmacokinetic curves of the test dosage forms (T1, T2 and T3) and the reference dosage form (R).

An open label, balanced, randomized, four-treatment, four-sequence, four period, oral comparative bioavailability study was made on healthy adult subjects with capsules comprising 90% E15-2, 90% E15-4 or 90% E15-6 extended release pellets and 10% immediate release pellets as test dosage forms (T1, T2 and T3) and VIMPAT® immediate release tablets as the reference listed drug (R). Under fasting conditions, the test dosage forms (T1, T2 and T3) were administered once daily at a dose of 400 mg, and the reference listed drug (R) was administered twice daily at a dose of 200 mg each time. The single dose pharmacokinetic parameters obtained are shown in table 31, and the pharmacokinetic curves are shown in FIG. 9.

TABLE 31

Single dose pharmacokinetic parameters.

| Formulation | $C_{max}$ (ug/mL) | $T_{max}$ (hr) | $AUC_{(0-t)}$ (hr*ug/mL) | $AUC_{(0-inf)}$ (hr*ug/mL) | $t_{1/2}$ (hr) | Ratio T/R ($AUC_{(0-inf)}$) |
|---|---|---|---|---|---|---|
| R | 9.12 | 13.16 | 240.5 | 254.8 | 14.71 | — |
| T1 | 8.07 | 8.44 | 237.0 | 248.7 | 14.45 | 0.98 |
| T2 | 7.23 | 13.38 | 238.9 | 253.3 | 14.71 | 0.99 |
| T3 | 6.56 | 16.48 | 231.1 | 245.1 | 14.81 | 0.96 |

Example 18—Simulation of Steady-State Pharmacokinetics by GastroPlus

Figure 10:
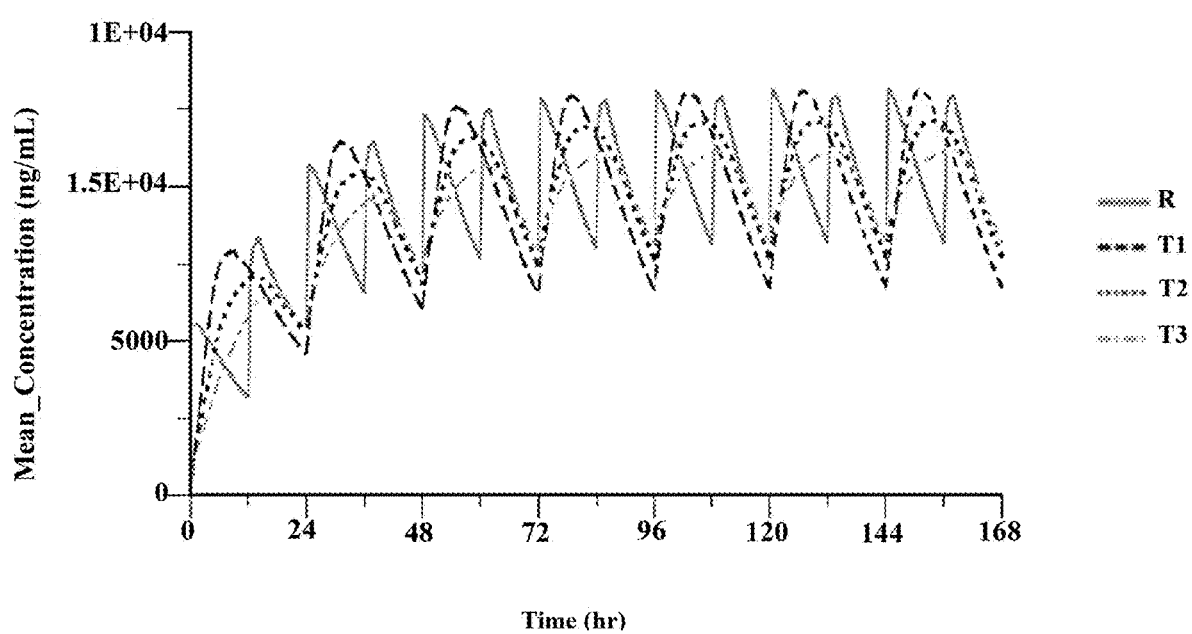
FIG. 10 illustrates the simulation results of the steady-state pharmacokinetic curves of the test dosage forms (T1, T2 and T3) and the reference dosage form (R).

Based on the pharmacokinetic data of the bioavailability study in Example 17, the steady-state $AUC_{ss}$, $C_{ss,max}$ and $C_{ss,min}$ of these dosage forms were simulated and predicted by using the pharmacokinetic software Gastroplus. The simulation results of steady-state pharmacokinetic parameters are shown in table 32, and the simulation results of steady-state pharmacokinetic curves are shown in FIG. 10. The result shows that the PTF of these lacosamide extended release capsules can be significantly reduced.

TABLE 32

Simulation of steady-state pharmacokinetic parameters.

| Formulation | Dose (mg) | $T_{max, ss}$ (h) | $C_{max, ss}$ (ug/mL) | $C_{min, ss}$ (ug/mL) | $AUC_{ss}$ (h*ug/mL) | PTF (%) |
|---|---|---|---|---|---|---|
| R | 200 | 1.00 | 13.89 | 7.73 | 125.8 | 58.8 |
| T1 | 400 | 7.03 | 13.24 | 6.81 | 248.0 | 31.1 |

TABLE 32-continued

Simulation of steady-state pharmacokinetic parameters.

| Formulation | Dose (mg) | $T_{max, ss}$ (h) | $C_{max, ss}$ (ug/mL) | $C_{min, ss}$ (ug/mL) | $AUC_{ss}$ (h*ug/mL) | PTF (%) |
|---|---|---|---|---|---|---|
| T2 | 400 | 10.06 | 12.28 | 7.78 | 252.7 | 42.7 |
| T3 | 400 | 12.91 | 11.31 | 8.26 | 244.3 | 30.0 |

What is claimed is:

1. A dosage form of lacosamide or a pharmaceutically acceptable salt thereof, comprising:
   (a) a first plurality of the particulates, each comprising
       i. a core comprising lacosamide or a pharmaceutically acceptable salt thereof, and
       ii. an extended release layer enclosing the core, wherein the extended release layer is free from lacosamide or a pharmaceutically acceptable salt thereof and comprises an extended release agent which is pH independent; wherein the core is free from the extended release agent, and
   (b) an immediate release portion of lacosamide or a pharmaceutically acceptable salt thereof in the form of a second plurality of particulates, wherein the lacosamide or the pharmaceutically acceptable salt thereof of the immediate release portion ranges from about 5% to about 30% by weigh in the total amount of the lacosamide or the pharmaceutically acceptable salt thereof in the dosage form,
wherein the dosage form is configured to have an in-vitro dissolution according to the following:
(a) less than about 20% in 1 hour;
(b) about 20%-80% in 4 hours; and
(c) more than about 80% in 12 hours; wherein the dissolution is determined using a USP type 1 dissolution system (Basket Apparatus) at 100 rpm and a temperature of 37±0.5° C. in 900 ml of pH 6.8 phosphate buffer for 12 hours.

2. The dosage form of claim 1, wherein the core comprises an inert inner core and an outer layer enclosing the inner core, and the lacosamide or a pharmaceutically acceptable salt thereof in (a) is disposed in the outer layer of the core.

3. The dosage form of claim 1, wherein lacosamide or a pharmaceutically acceptable salt thereof in the dosage form has an in-vitro dissolution according to the following:
(a) from about 11% to about 18% in 1 hour,
(b) from about 20% to about 35% in 2 hours,
(c) from about 40% to about 70% in 4 hours,
(d) from about 65% to about 95% in 6 hours, and
(e) more than about 90% in 12 hours,
wherein the in-vitro dissolution is determined using a USP type 1 dissolution system (Basket Apparatus) at 100 rpm and a temperature of 37±0.5° C. in 900 ml of pH 6.8 phosphate buffer for 12 hours.

4. The dosage form of claim 1, wherein the amount of lacosamide or a pharmaceutically acceptable salt thereof dissolved in the first two hours is about 1.5-2.0 times more than the amount dissolved in the first one hour, and the amount of lacosamide or a pharmaceutically acceptable salt thereof dissolved in the first four hours is about 1.7-2.2 times more than the amount dissolved in the first two hours, and the amount of lacosamide or a pharmaceutically acceptable salt thereof dissolved in the first six hours is about 1.7-2.2 times more than the amount dissolved in the first three hours.

5. The dosage form of claim 4, wherein the amount of lacosamide or a pharmaceutically acceptable salt thereof dissolved by 6th hour ranges from about 72% to about 90% of the total amount of lacosamide or a pharmaceutically acceptable salt thereof in the dosage form.

6. The dosage form of claim 1, wherein the total amount of lacosamide or a pharmaceutically acceptable salt thereof ranges from about 40% to about 80% by weight in the dosage form.

7. The dosage form of claim 1, wherein the extended release agent ranges from about 5% to about 30% by weight in the extended release portion.

8. The dosage form of claim 1, wherein a ratio between the lacosamide or a pharmaceutically acceptable salt thereof in the first plurality of the particulates and the extended release agent ranges from about 15:1 to about 1:1.

9. The dosage form of claim 1, wherein the total amount of lacosamide or a pharmaceutically acceptable salt thereof in the dosage form ranges from about 20 mg to about 600 mg.

10. The dosage form of claim 1, wherein the pH independent extended release agent is selected from the group consisting of ethyl cellulose, methyl cellulose, cellulose acetate, polyvinyl acetate, ethyl acrylate/methyl methacrylate/trimethylamino ethyl methacrylate chloride copolymer, ethyl acrylate/methyl methacrylate/trimethylamino ethyl methacrylate chloride copolymer, and any mixtures thereof.

11. The dosage form of claim 1, wherein the pH independent extended release agent is ethyl cellulose.

12. The dosage form of claim 1, wherein the dosage form contains lacosamide only in salt free form, and wherein the lacosamide of the immediate release portion ranges from about 5% to about 15% by weigh in the total amount of lacosamide in the dosage form.

13. The dosage form of claim 1, where the first plurality of particulates have an average diameter ranging from about 300 μm to about 1400 μm.

14. The dosage form of claim 1, wherein the dosage form when orally administered once daily achieves more than 90% of the $AUC_{(0\text{-}inf)}$ of an immediate released reference lacosamide administered to the subject in fasting condition, wherein the daily dosage of the dosage form is the same as the daily dosage of the immediate released reference lacosamide.

15. A method of providing an extended release of lacosamide in a subject, comprising administering to the subject a dosage form of claim 1, wherein the amount of the lacosamide or the pharmaceutically acceptable salt thereof and the amount of the pH independent extended release agent are selected so that the dosage form provides an in-vitro dissolution according the following:
(a) from about 11% to about 18% in 1 hour,
(b) from about 20% to about 35% in 2 hours,
(c) from about 40% to about 70% in 4 hours,
(d) from about 65% to about 95% in 6 hours, and
(e) more than about 90% in 12 hours,
wherein the in-vitro dissolution is determined using a USP type 1 dissolution system (Basket Apparatus) at 100 rpm and a temperature of 37±0.5° C. in 900 ml of pH 6.8 phosphate buffer for 12 hours.

16. The method of claim 15, wherein the dosage from is administered once a day.

17. A method of treating a neurological or psychiatric disease or condition, comprising administering to a subject in need thereof a dosage of claim 1.

18. The method of claim 17, wherein the disease or condition is selected from the group consisting of epilepsy, migraine, essential tremor, restless limb syndrome, cluster headache, neuralgia, neuropathic pain, Tourette's syndrome, infantile spasm, anxiety, bipolar disorder, psychosis, mania, schizophrenia, depression, dementia, autism, obsessive compulsive disorder, post-traumatic stress disorder, attention deficit hyperactivity disorder, impulse control disorder, borderline personality disorder, addiction, chronic neurodegenerative disorder, acute neurodegeneration, and amyotrophic lateral sclerosis.

19. The method of claim 17, wherein the disease or condition is epilepsy.

* * * * *